(12) United States Patent
Stevenson

(10) Patent No.: US 6,456,481 B1
(45) Date of Patent: Sep. 24, 2002

(54) INTEGRATED EMI FILTER-DC BLOCKING CAPACITOR

(75) Inventor: Robert A. Stevenson, Canyon Country, CA (US)

(73) Assignee: Greatbatch-Sierra, Inc., Clarence, NY (US)

( * ) Notice: Subject to any disclaimer, the term of this patent is extended or adjusted under 35 U.S.C. 154(b) by 0 days.

(21) Appl. No.: 09/872,092

(22) Filed: May 31, 2001

(51) Int. Cl.$^7$ ................................................ H01G 4/35
(52) U.S. Cl. ...................... 361/302; 361/306.1; 361/303
(58) Field of Search .................. 361/302, 303, 361/328, 329, 330, 306.1, 306.2, 306.3, 307; 333/182, 184, 185

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,424,551 A | 1/1984 | Stevenson et al. |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |

(List continued on next page.)

OTHER PUBLICATIONS

Dual Electrode Plate MLC for High Voltage Pulse Applications, Capacitor and Resistor Technology Symposium (CARTS), Huntington Beach, California, Mar. 6–10, 2000.
Title: A Capacitor's Inductance: Critical Property for Certain Applications, IEEE 49th Electronic Components & Technology Conference (IEEE–ECTC), San Diego, California, Jun. 1–4, 1999.
Title: Design and Application of Broadband Ceramic Feed–Through Capacitor EMI Filters to Cardiac Pacemakers and Implantable Defibrillators, Robert A. Stevenson, P.E., 5 pages, Oct. 30 to Nov. 2, 1997.
Title: Radically New Internally Grounded Feedthrough Capacitor, Bob Stevenson and Rick Brendel, 8 pages, Mar. 25–30, 2001.

*Primary Examiner*—Anthony Dinkins
(74) *Attorney, Agent, or Firm*—Scott W. Kelley; Kelly Bauerfeld Lowry & Kelley, LLP

(57) ABSTRACT

An integrated electromagnetic interference (EMI) filter capacitor and DC blocking capacitor is provided in a single monolithic casing of ceramic dielectric material. First and second sets of electrode plates are disposed within the monolithic casing to form the DC blocking capacitor, and ground electrode plates are disposed between selected portions of the first and second sets of electrode plates to form the EMI filter. In several of the embodiments, the first and second sets of electrode plates form a plurality of distinct DC blocking capacitors. The ground electrode plates cooperatively form, with the first and second sets of electrode plates, EMI filters for each of the distinct DC blocking capacitors. Discontinuous lead wires may be provided which extend at least partially into the casing, wherein a first segment of the lead wire is conductively coupled to the first set of electrode plates, and a second set of the lead wire is conductively coupled to the second set of electrode plates. Grounded shields also may be co-planarly disposed between adjacent components of the first and second sets of electrode plates to reduce cross-talk therebetween.

56 Claims, 30 Drawing Sheets

U.S. PATENT DOCUMENTS

| | | |
|---|---|---|
| 5,440,447 A | 8/1995 | Shipman et al. |
| 5,670,063 A | 9/1997 | Hegner et al. |
| 5,751,539 A | 5/1998 | Stevenson et al. |
| 5,825,608 A | 10/1998 | Duva et al. |
| 5,905,627 A | 5/1999 | Brendel et al. |
| 5,959,829 A | 9/1999 | Stevenson et al. |
| 5,973,906 A * | 10/1999 | Stevenson et al. .......... 361/302 |
| 5,978,204 A | 11/1999 | Stevenson |

* cited by examiner

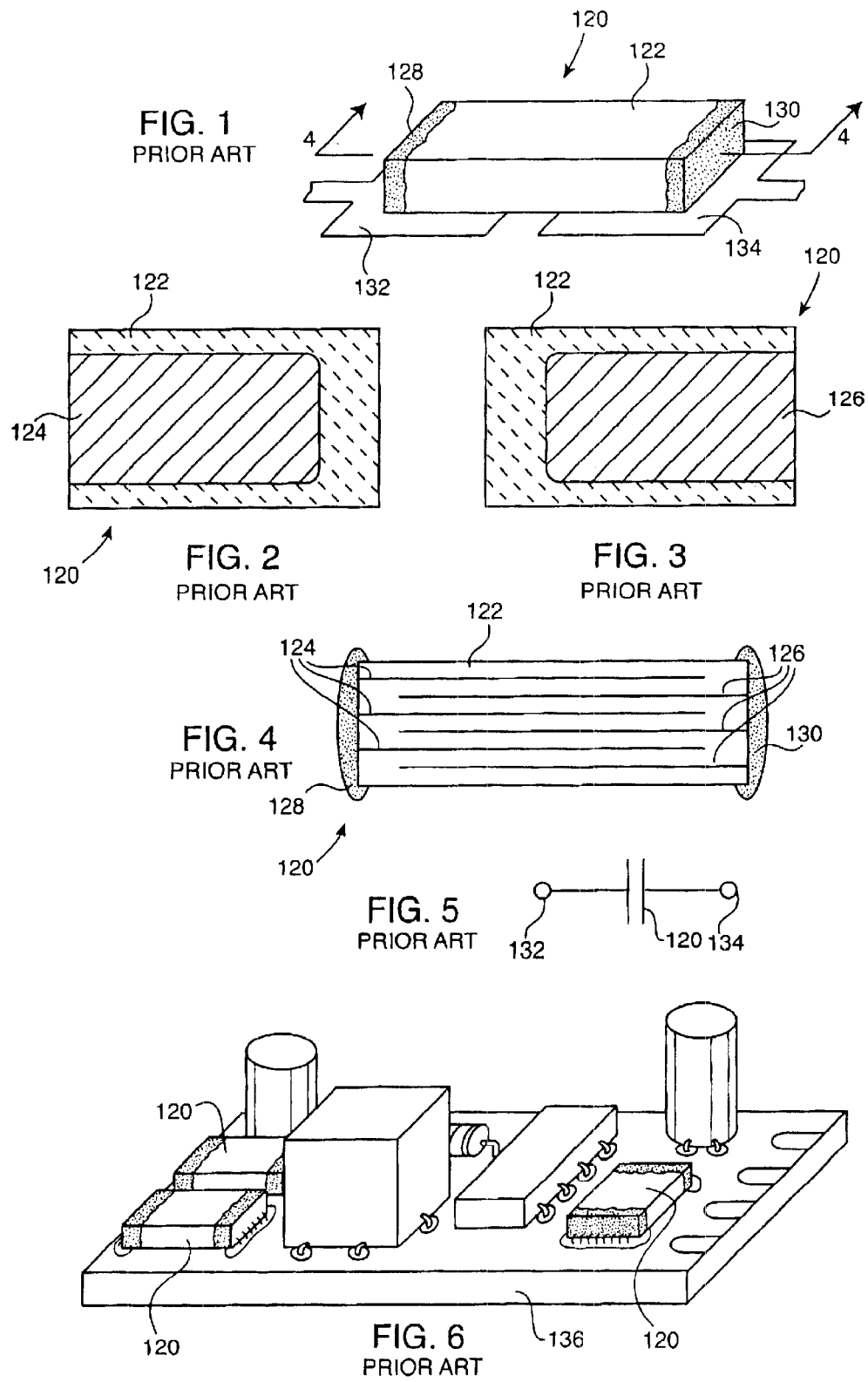

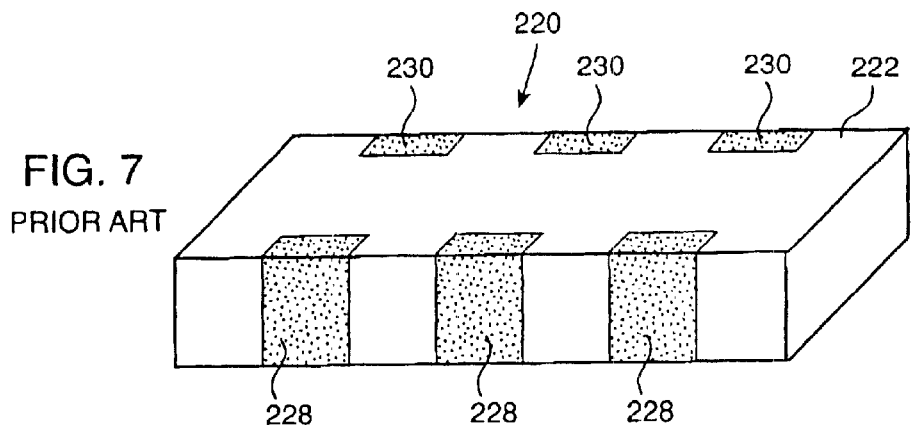
FIG. 7
PRIOR ART
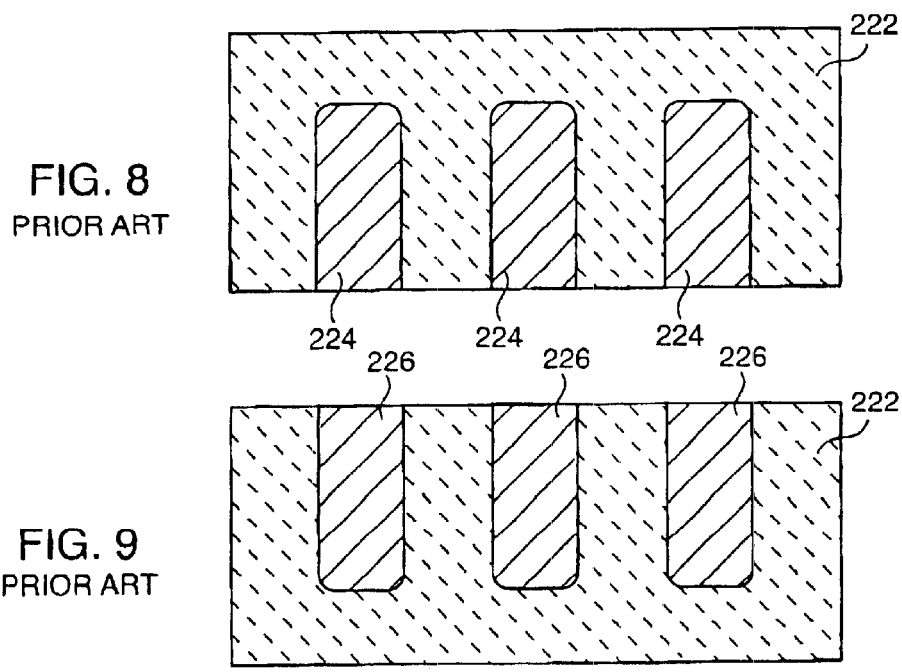
FIG. 8
PRIOR ART
FIG. 9
PRIOR ART
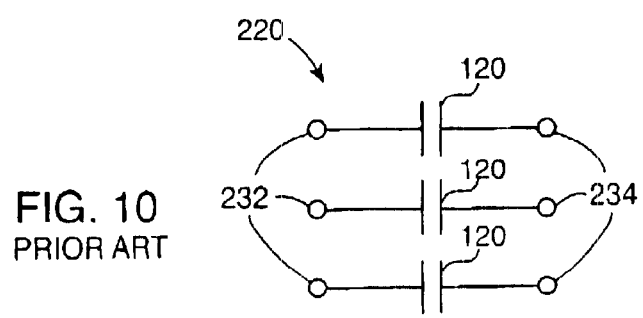
FIG. 10
PRIOR ART

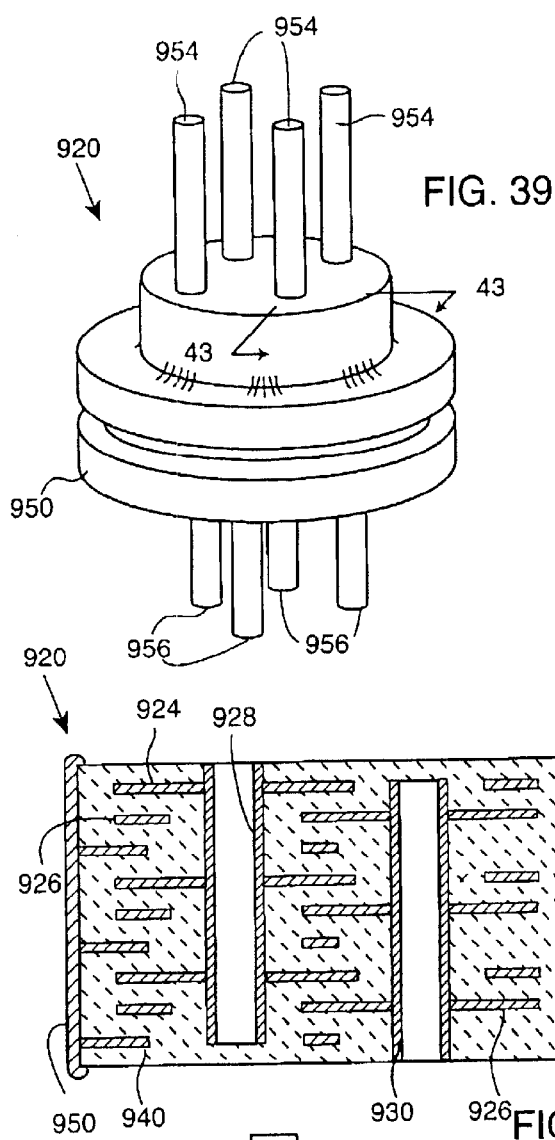
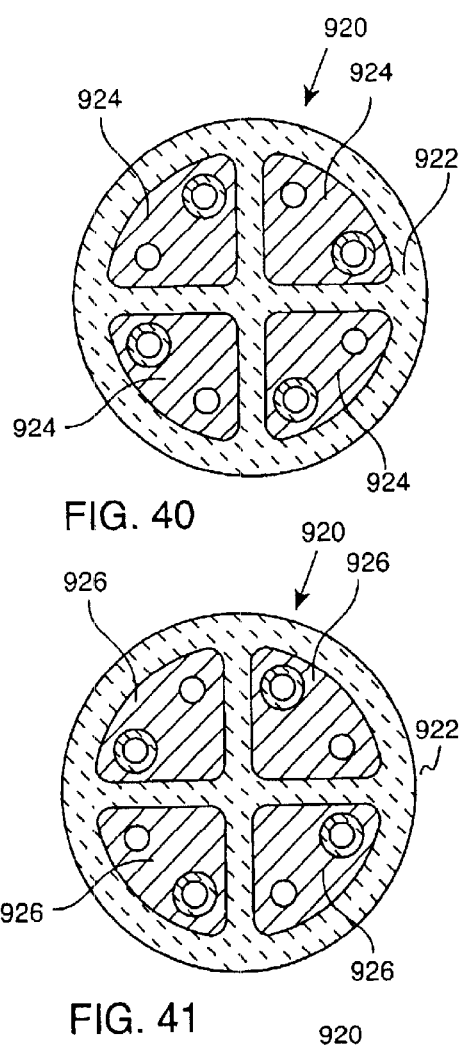
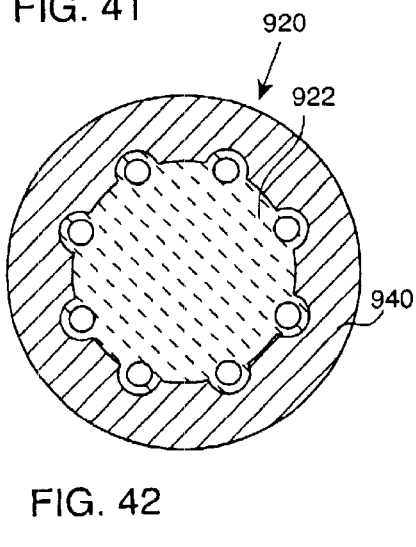
FIG. 39
FIG. 40
FIG. 41
FIG. 42
FIG. 43
FIG. 44

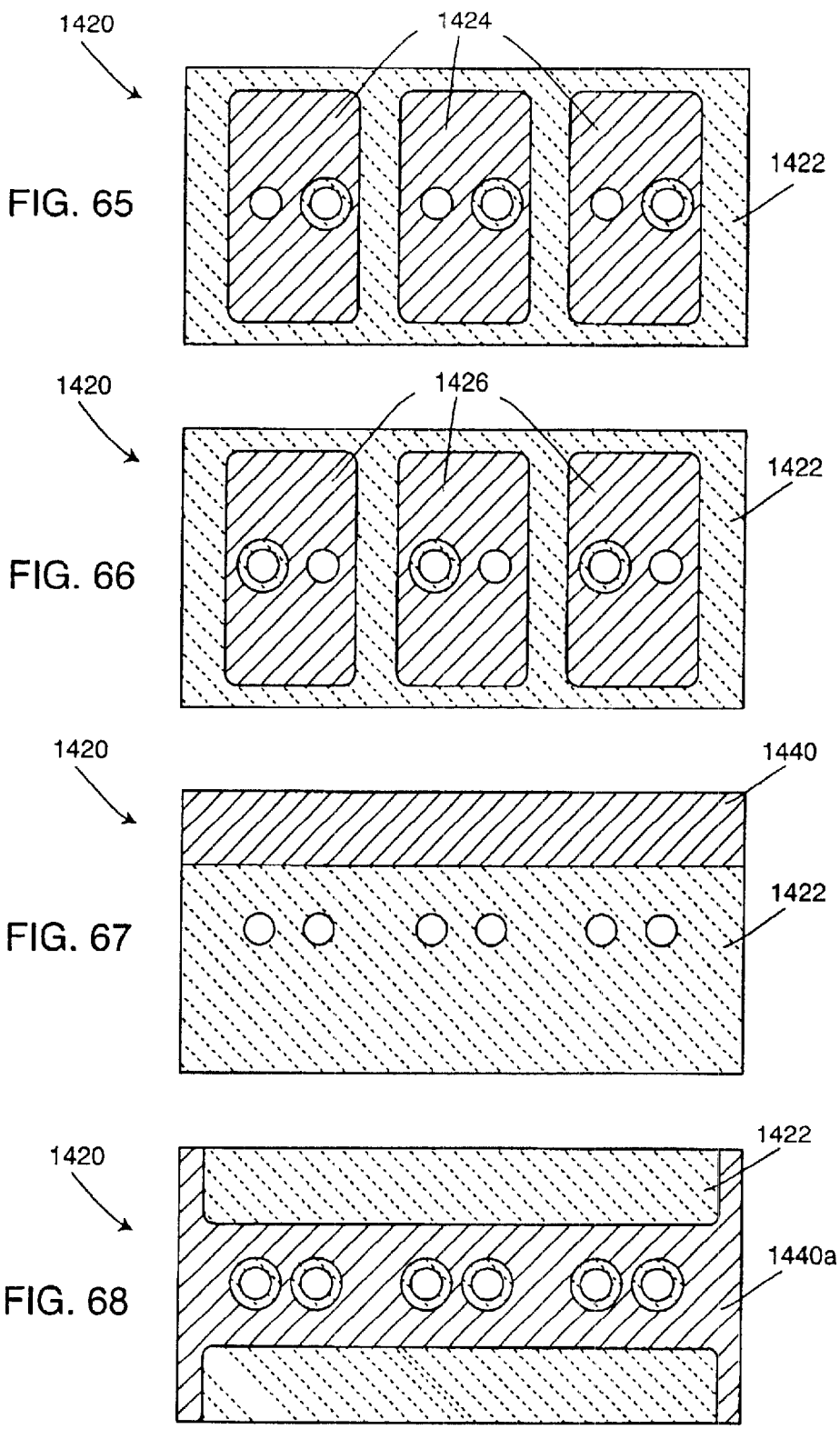

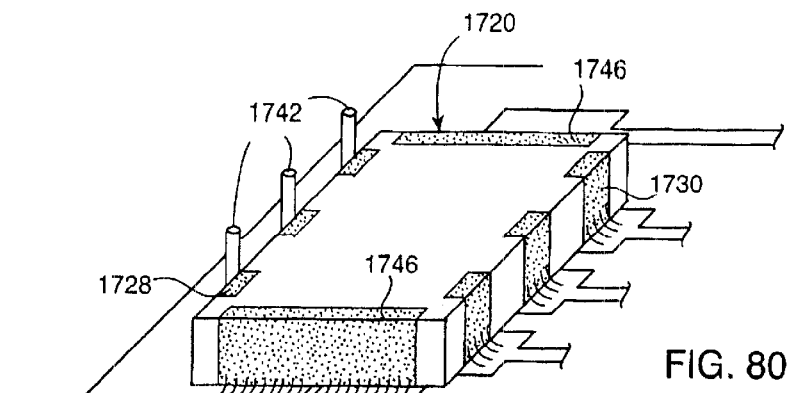
FIG. 80
FIG. 81
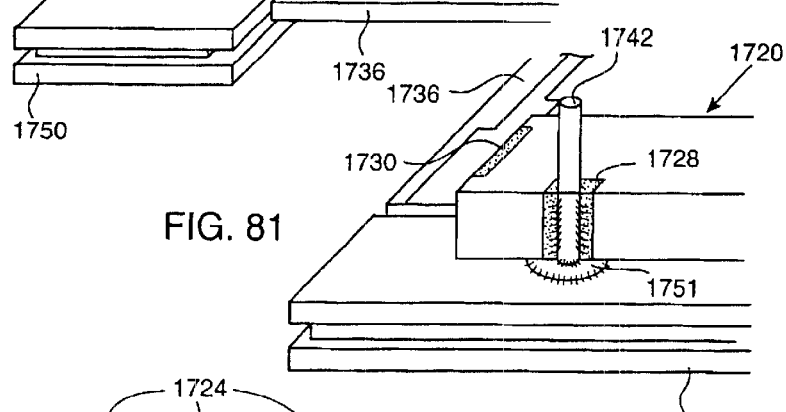
FIG. 82
FIG. 83
FIG. 84

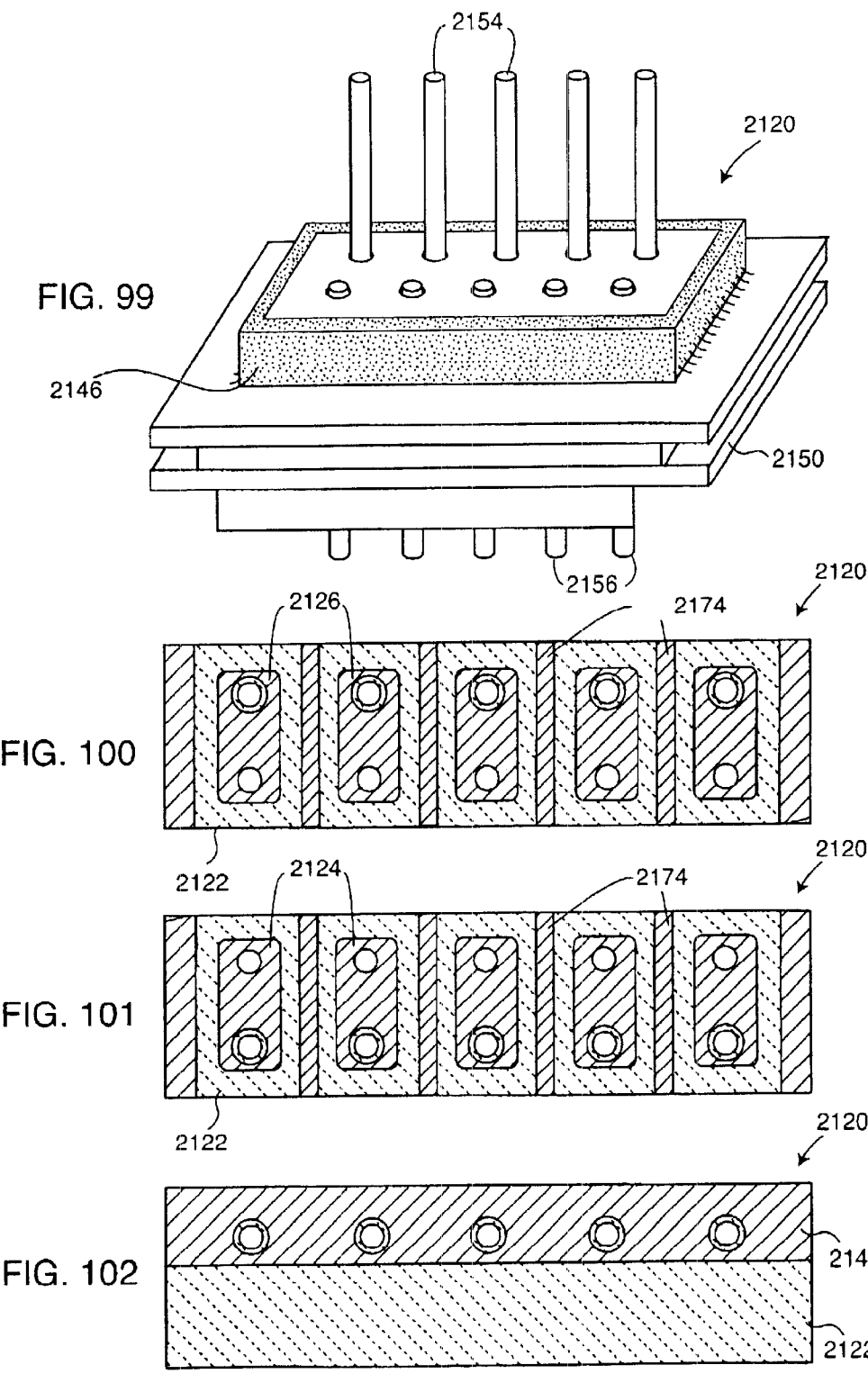

INTEGRATED EMI FILTER-DC BLOCKING CAPACITOR

BACKGROUND OF THE INVENTION

This invention relates generally to ceramic capacitors which provide DC blocking and EMI filter functions. More specifically, this invention relates to an integrated DC blocking capacitor and high frequency EMI filter in a monolithic ceramic housing.

There are two primary ceramic capacitor geometries in common use in the industry—the rectangular chip and the feedthrough (often called a discoidal capacitor). Ceramic capacitors are typically constructed by interleaving nonconductive layers of high dielectric constant ceramic material with metallic electrodes. The metallic electrodes are typically "laid-down" on the green ceramic material by silk screening processes. The device is then fired (sintered) to form a rugged monolithic structure (the "capacitor"). Monolithic ceramic capacitors are well known in the art for a variety of applications in both surface mount (chip capacitor) and leaded applications. Also well known in the art are stacked film capacitors, which are constructed in a very similar manner to ceramic chip capacitors. Layers of film dielectric are interleaved with conductive electrodes, thereby forming a chip-type capacitor.

The ceramic monolithic chip (MLC) capacitor (or "chip capacitor") is produced in very high commercial volumes in highly automated facilities. Over the years the cost of ceramic chip capacitors has dropped a great deal. It is now common to purchase certain value chip capacitors for only a few pennies. The ceramic feedthrough capacitor is only produced in a small fraction of the chip capacitor volume. Accordingly, feedthrough capacitor production has not been nearly as automated. In addition, the feedthrough capacitor is inherently more expensive to produce due to drilling and centering the through hole, tighter dimensional control, reduced volumetric efficiency and difficulty in automating the manufacturing process. Typically the cost of a particular value chip capacitor is ten to twenty percent of the cost of an equivalent value discoidal feedthrough capacitor.

FIGS. 1 through 4 illustrate a prior art conventional MLC chip capacitor 120. The chip capacitor 120 is of standard construction, including a ceramic dielectric 122 that has disposed therein alternating lay up patterns for a first set of electrode plates 124 and a second set of electrode plates 126 separated by the ceramic dielectric 122 (FIGS. 2 through 4). The first set of electrode plates 124 terminates in a first metallization band 128 exposed at one end of the chip capacitor 120, and the second set of electrode plates 126 is conductively coupled to a second metallization band 130 disposed at an opposite end of the chip capacitor 120. The chip capacitor 120 acts as a two terminal device. That is, it is connected from one circuit trace 132 to another circuit trace 134, or from a circuit trace to ground, in order to decouple or filter signals from one line to a reference point. In the embodiment of FIGS. 1 through 4, the metallization bands 128 and 130 are soldered or otherwise conductively coupled to pads for the circuit traces 132 and 134 as shown.

FIG. 5 is an electrical schematic diagram of the chip capacitor 120 of FIGS. 1–4 illustrating its DC blocking capacitor capability. FIG. 6 is an exemplary illustration of a circuit board 136 having three of the chip capacitors 120 mounted thereon, together with other electronic components.

FIGS. 7 through 9 illustrate a prior art integrated chip capacitor 220 wherein three individual chip capacitors 120 have been incorporated into a single monolithic block 222. In the descriptions that follow, functionally equivalent elements of the various illustrated embodiments are referred to by the same reference number in increments of 100. Accordingly, the chip capacitor 220 is of a standard construction, including a ceramic dielectric 222 that has disposed therein alternating lay-up patterns of a first set of electrode plates 224 and a second set of electrode plates 226 separated by the ceramic dielectric 222 (FIGS. 8 and 9). The first set of electrode plates 224 terminates in first metallization bands 228 exposed along one side of the chip capacitor 220, and the second set of electrode plates 226 is conductively coupled to respective second metallization bands 230 disposed at an opposite side of the chip capacitor 220. Each of the chip capacitors 120 within the monolithic block 222 is connected from one respective circuit trace 232 to another respective circuit trace 234 (FIG. 10), or from a circuit trace to ground, in order to decouple or filter signals from one line to a reference point. Such monolithic ceramic chip capacitors, also known as "chips" or DC blocking capacitors, are used in a myriad of applications, for example, in RF bypass, energy storage, and many other applications.

Feedthrough terminal or discoidal capacitor assemblies are generally well known for connecting electrical signals through the housing or case of an electronic instrument. For example, in implantable medical devices such as cardiac pacemakers, defibrillators, or the like, the terminal pin assembly comprises one or more conductive terminal pins supported by an insulator structure for feedthrough passage from the exterior to the interior of the medical device. Many different insulator structures and related mounting methods are known for use in medical devices wherein the insulator structure provides a hermetic seal to prevent entry of body fluids into the housing of the medical device. However, the feedthrough terminal pins are typically connected to one or more lead wires which effectively act as an antenna and thus tend to collect stray electromagnetic interference (EMI) signals for transmission into the interior of the medical device. In prior devices, such as those shown in U.S. Pat. Nos. 5,333,095 and 4,424,551 (the contents of which are incorporated herein), the hermetic terminal pin subassembly has been combined in various ways with a ceramic feedthrough capacitor filter to decouple electromagnetic interference (EMI) signals into the housing of the medical device.

With reference to FIGS. 11–13, in a typical prior art unipolar feedthrough filter assembly (as described in U.S. Pat. No. 5,333,095), a round/discoidal (or rectangular) ceramic feedthrough filter capacitor 320 is combined with a hermetic terminal pin assembly to suppress and decouple the undesired interference or noise transmission along a terminal pin (not shown). The feedthrough capacitor 320 is coaxial, having two sets of electrode plates 338, 340 embedded in spaced relation within an insulative dielectric substrate or base 322, formed typically as a ceramic monolithic structure. One set of the electrode plates (active) 338 is electrically connected in parallel to a cylindrical metallized area at an inner diameter cylindrical surface of the coaxial capacitor structure and then to a conductive terminal pin 342 utilized to pass the desired electrical signal or signals. A second or ground set of electrode plates 340 is coupled in parallel at an outer diameter surface of the discoidal capacitor 320 to a cylindrical ferrule of conductive material (330), which is electrically connected in turn to the conductive housing of the electronic device. The number and dielectric thickness spacing of the electrode plate sets 338 and 340 varies in accordance with the capacitance value measured in microfarads or picofarads and the voltage rating of the coaxial capacitor 320. The ground electrode plates 340 are coupled in parallel together by a metallized layer 330 which is either fired, sputtered or plated onto the ceramic capacitor. The metallized band 330, in turn, is coupled to the ferrule by conductive adhesive, soldering, brazing, welding, or the like. Similarly, the active electrode plates 328 are coupled in parallel together by a metallized layer 328 which is either glass fit fired or plated onto the ceramic capacitor. This metallized band 328, in turn, is mechanically and electrically coupled to the leads wire(s) by conductive adhesive, soldering or the like.

In operation, the coaxial capacitor 320 permits passage of relatively low frequency electrical signals along the terminal pin 342, while shielding and decoupling/attenuating undesired interference signals of typically high frequency (such as EMI from cellular telephones or microwave ovens) to the conductive housing.

As can be seen in FIG. 13, the feedthrough capacitor 320 is a three-terminal device as opposed to a chip capacitor, which is only a two terminal device. It is because of the nature of coaxial three-terminal capacitor devices that broad band EMI filtering is accomplished through the transmission line effect. Feedthrough capacitors of this general type are available in unipolar (one), bipolar (two), tripolar (three), quad polar (four), pentapolar (five), hexpolar (six), and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy which is electrically and mechanically coupled to the hermetic terminal pin assembly, which is in turn electrically coupled to the coaxial feedthrough filter capacitor 320. As a result, the filter capacitor and terminal pin assembly prevents or attenuates entrance of interference signals to the interior of the pacemaker housing, wherein such interference signals could otherwise adversely affect the desired cardiac pacing or defibrillation function.

FIGS. 14–17 illustrate a prior art flat-thru style capacitor 420. Flat-thru capacitors 420 are three-terminal devices similar to the feedthrough capacitor 320 as they are best modeled as a transmission line and also exhibit excellent high frequency performance. Flat-thru capacitors 420 are well suited for substrate or circuit board mounting, however, they are very limited in the amount of current that they can handle. This is because the circuit current must pass entirely through the electrodes themselves which are thin and lacy. In general, the flat-thru design is not used in high current applications, such as the output circuitry of an implantable defibrillator or a switch mode power supply, because of these current limitations.

The flat-through capacitor 420 includes a ceramic dielectric 422 that has disposed therein alternating lay-up patterns for an active set of electrode plates 438 and a ground set of electrode plates 440 separated by the ceramic dielectric 422. The active set of electrode plates 438 terminates in metallization bands 428a and 428b exposed at opposite ends of the flat-through capacitor 420. The ground set of electrode plates 440 is similarly conductively coupled to second metallization bands 430a and 430b disposed in a continuous band all around the opposite sides of the flat-through capacitor 420. The first metallization bands 428a and 428b are connected from one circuit trace 432 to another circuit trace 434. The circuit traces 432 and 434 comprise a circuit for conducting DC, analog, pulse or RF current. The second metallization bands 430a and 430b are connected to a circuit trace 444 which serves as a ground plane.

Operation of the flat-through capacitor 420 is similar to the discoidal capacitor 320 described previously in that the flat-through capacitor 420 permits passage of DC or relatively low frequency electrical signals along the active set of electrode plates 438, while decoupling/attenuating undesired interference signals of typically high frequency (such as EMI from cellular telephones or microwave ovens) to the conductive ground plane 444.

With reference to FIG. 17, it will be noted that the electrical schematic for the flat-through capacitor 420 of FIG. 14 is a three-terminal device which is identical to the electrical schematic for the discoidal/feedthrough capacitor 320 as illustrated in FIG. 13.

FIGS. 18–21 illustrate a prior art integrated flat-through style capacitor 520 wherein three individual flat-through capacitors 420 have been incorporated into a single monolithic block 522. In this regard, the integrated flat-through capacitor 520 is of a standard construction, including a ceramic dielectric 522 that has disposed therein alternating lay-up patterns for active set of electrode plates 538 and a ground set of electrode plates 540 separated by the ceramic dielectric 522. The active set of electrode plates 538 terminate in metallization bands 528a and 528b exposed at opposite ends of the integrated flat-through capacitor 520. The ground set of electrode plates 540 are similarly conductively coupled to second metallization bands 530a and 530b disposed on opposite sides of the flat-through capacitor 520. The first metallization bands 528a and 528b are conductively coupled from one respective circuit trace 532 to another respective circuit trace 534 which comprise individual circuits for conducting RF current. The second metallization bands 530a and 530b are connected to a circuit trace 540 which serves as a ground plane.

Operation of the integrated flat-through capacitor 520 is similar to the capacitor 420 discussed above in that the flat-through capacitor 520 permits passage of relatively low frequency electrical signals along three distinct active set of electrode plates 538, while shielding and decoupling/attenuating undesired interference signals of typically high frequency (such as EMI from cellular telephones or microwave ovens) to the conductive ground plane 540.

Since chip capacitors are used for circuit coupling and decoupling, they also provide a path where undesirable signals can be coupled. Electromagnetic interference (EMI) is a very serious concern as it can disrupt or even cause a complete malfunction of an electronic device. Chip capacitor EMI filters are relatively ineffective at high frequency in that they offer too much series inductance and therefore self resonate at a relatively low frequency.

In the past, it is common to employ monolithic ceramic feedthrough capacitors either in a rectangular or circular planar array. Where only one lead wire is involved one may use a unipolar or discoidal feedthrough capacitor. The feedthrough capacitor is a unique device in that it forms a transmission line. Accordingly, because of the geometry of the feedthrough capacitor it is effective at attenuating EMI signals over a very broad frequency range. The feedthrough capacitor does not exhibit the undesirable large value series inductance that a chip capacitor exhibits. Because of this, the feedthrough capacitor device resonates at a relatively high frequency and also continues to perform very well at above this resonant frequency. As discussed above, another form of feedthrough capacitor is known as the "Flat-thru" capacitor. With the "Flat-thru" capacitor, circuit currents pass through the capacitor itself between an opposed set of ground plates. This is also a very efficient EMI filter device, which does not series resonate in the way that a chip capacitor does.

It is common in the art to protect an electronic device or housing from the effects of electromagnetic interference by providing on each lead wire at the point of ingress or egress of the electromagnetic shield a feedthrough capacitor or a "flat-thru" capacitor. It is then typical to route the wires to a substrate or circuit board where DC coupling capacitors are used. This isolates the electronic device from the "outside world" and provides protection in that DC bias would not be able to damage body tissue in the case of a cardiac pacemaker.

It will be appreciated, then, that there is a need for both feedthrough capacitor EMI filters and monolithic ceramic chip capacitors in selected applications. In the past, these have always been two separate and discreet components. A disadvantage of using both a feedthrough capacitor in combination with a number of discrete DC blocking capacitors is that this increases the size and the cost of an electronic assembly.

Accordingly, there is a need for a new electronic component which integrates both a feedthrough capacitor and a DC blocking capacitor into a single package. By integrated these devices into a single package, the number of components and the number of piece parts is reduced. Moreover, the volumetric efficiency is improved. The present invention fulfills this need and provides other related advantages.

SUMMARY OF THE INVENTION

The present invention comprises an integrated ceramic feedthrough filter capacitor and DC blocking capacitor in a single monolithic unit. This assembly provides for a series coupling capacitor, known as the DC blocking capacitor, which is integrated with a feedthrough capacitor or "Flat-Thru" capacitor. Series coupling capacitors are used in a wide variety of electronics applications to isolate one circuit from another at DC frequencies. A property of the DC coupling capacitor is that it presents a relatively low impedance at high frequencies. This makes it possible for undesirable electromagnetic interference (EMI) signals to enter into the device and cause malfunction of the electronic circuitry. The integrated device, as described herein, incorporates the properties of a DC blocking capacitor, but also includes a highly efficient high frequency EMI filter in order to protect the device from the unwanted effects of EMI. The present invention is particularly suited for use in human implantable applications, which typically employ a DC blocking capacitor on all tissue stimulation circuits. This DC blocking capacitor is mandated by the Federal Food and Drug Administration (FDA) in order to prevent damage to tissue in implantable medical devices such as cardiac pacemakers, implantable defibrillators, neurostimulators, cochlear implants and the like. All of these devices are also sensitive to EMI, such as that caused by a cellular telephone or other emitter. The present invention effectively provides DC blocking while at the same time filtering out undesirable EMI.

The integrated capacitor of the present invention comprises, generally, a monolithic casing of ceramic dielectric material, first and second sets of electrode plates disposed within the monolithic casing to form a DC blocking capacitor, and ground electrode plates disposed within the monolithic casing and between selected portions of the first and second sets of electrode plates to form an electromagnetic interference (EMI) filter. A first conductive band is provided on a surface of the casing for conductively coupling the first set of electrode plates, a second conductive band is also provided on a surface of the casing for conductively coupling the second set of electrode plates, and a third conductive band is provided on a surface of the casing for conductively coupling the ground electrode plates. These conductive bands may be disposed on either interior or exterior surfaces of the casing.

The first and second sets of electrode plates may include an induction-inducing material such as nickel to obtain desired electrical characteristics.

A discontinuous lead wire may be provided which extends at least partially into the casing. A first segment of the lead wire is conductively coupled to the first set of electrode plates, and a second segment of the lead wire is conductively coupled to the second set of electrode plates. An insulative spacer may be disposed between abutting ends of the first and second segments of the lead wire within the casing, or the segments thereof may be offset from one another. The ground electrode plates are typically conductively coupled to a conductive ferrule through which a portion of the lead wire extends in non-conductive relation.

In several of the illustrated embodiments, an integrated electromagnetic interference (EMI) filter-DC blocking capacitor is provided which includes a casing of dielectric material having generally parallel first and second sets of electrode plates disposed therein which form a plurality of distinct DC blocking capacitors, and a set of generally parallel ground electrode plates disposed within the casing between selected portions of adjacent plates of the first and second sets of electrode plates. The ground electrode plates cooperatively form, with the first and second sets of electrode plates, a EMI filter for each of the distinct DC blocking capacitors.

The aforementioned conductive bands may be provided on external surfaces of the casing for conductively coupling the ground electrode plates to the conductive ferrule, or on an internal surface. In such case, a ground pin is typically conductively coupled to the ferrule and the conductive band. The ends of the first and second segments of the lead wire may be disposed in passageways provided in the casing. The passageways may comprise through holes wherein an end of each of the first and second segments is covered with a non-conductive cap.

The ground electrode plates may be aligned with the lead wires extending into the casing or offset from the lead wires.

In alternative embodiments, the ground electrode plates may comprise a first set of ground electrode plates which are co-planar with the first set of electrode plates, and a second set of ground electrode plates which are co-planar with the second set of electrode plates. A third set of electrode plates may be provided which form an EMI filter, cooperatively with the ground electrode plates, for a lead wire extending through the casing and conductively coupled to the third set of electrode plates. Moreover, grounded shield electrode plates may be co-planarly disposed between adjacent components of the first and second sets of electrode plates to reduce cross-talk therebetween.

Other features and advantages of the present invention will become apparent from the following, more detailed description taken in conjunction with the accompanying drawings, which illustrate by way of example the principles of the invention.

BRIEF DESCRIPTION OF THE DRAWINGS

The accompanying drawings illustrate the invention. In such drawings:

FIG. 1 is a perspective view of a prior art conventional chip capacitor which is surface-mounted to circuit traces;

FIG. 2 is an exemplary horizontal section taken through the chip capacitor of FIG. 1, illustrating the configuration of a first set of electrode plates therein;

FIG. 3 is an exemplary horizontal section taken through the chip capacitor FIG. 1, illustrating the configuration of a second set of electrode plates therein;

FIG. 4 is a vertical section taken generally along the line 4—4 of FIG. 1;

FIG. 5 is an electrical schematic diagram of the chip capacitor of FIG. 1;

FIG. 6 is a perspective view of an exemplary substrate of a circuit board showing three of the chip capacitors of FIG. 1 mounted thereto with other electronic components;

FIG. 7 is a perspective view of a prior art integrated chip capacitor showing three conventional chip capacitors in a single monolithic block;

FIG. 8 is an exemplary horizontal section taken through the integrated chip capacitor of FIG. 7, illustrating the configuration of three distinct first sets of electrode plates therein;

FIG. 9 is an exemplary horizontal section similar to FIG. 8, illustrating the configuration of three distinct second sets of electrode plates;

FIG. 10 is an electrical schematic diagram of the integrated chip capacitor of FIGS. 7;

FIG. 39 is a perspective view of a quad polar integrated DC blocking-EMI filter capacitor mounted to a hermetic terminal;

FIG. 40 is an exemplary horizontal section taken through the quad polar integrated capacitor of FIG. 39, illustrating the configuration of a first set of electrode plates therein;

FIG. 41 is a horizontal section similar to FIG. 40, illustrating the configuration of a second set of electrode plates;

FIG. 42 is a horizontal section similar to FIGS. 40 and 41, illustrating the configuration of the set of ground electrode plates;

FIG. 43 is an enlarged, sectional view taken generally along the line 43—43 of FIG. 39;

FIG. 44 is an electrical schematic diagram of the quad polar integrated DC blocking-EMI filter capacitor of FIG. 39;

FIG. 65 is an exemplary horizontal section taken through the integrated capacitor of FIG. 62, illustrating the configuration of three distinct first sets of electrode plates therein;

FIG. 66 is a horizontal section similar to FIG. 65, illustrating the configuration of three distinct second sets of electrode plates;

FIG. 67 is a horizontal section similar to FIGS. 65 and 66, illustrating the configuration of one type of a set of ground electrode plates;

FIG. 68 is a sectional view similar to FIG. 67, illustrating an alternative arrangement for the set of ground electrode plates;

FIG. 80 is a partial perspective view of a hermetic terminal with three lead wires and an integrated capacitor of the subject invention disposed between the three lead wires and corresponding circuit board traces;

FIG. 81 is a perspective view of the assembly of FIG. 80 rotated 90 degrees;

FIG. 82 is an exemplary horizontal section taken through the capacitor of FIG. 80, illustrating the configuration of three distinct first sets of electrode plates therein;

FIG. 83 is a horizontal section similar to FIG. 82, illustrating the configuration of three distinct second sets of electrode plates;

FIG. 84 is a horizontal section similar to FIGS. 82 and 83, illustrating the configuration of a set of ground electrode plates;

FIG. 99 is a perspective view of a hermetic terminal of a cardiac pacemaker, implantable cardioverter defibrillator, neurostimulator or other implantable medical device, and a novel integrated capacitor embodying the present invention;

FIG. 100 is an exemplary horizontal section taken through the integrated capacitor FIG. 99, illustrating the configuration of five distinct first sets of electrode plates therein;

FIG. 101 is a horizontal section similar to FIG. 100, illustrating the configuration of five distinct second sets of electrode plates;

FIG. 102 is a horizontal section similar to FIGS. 100 and 101, illustrating the configuration of a set of ground electrode plates;

DETAILED DESCRIPTION OF THE PREFERRED EMBODIMENTS

Figure 22:
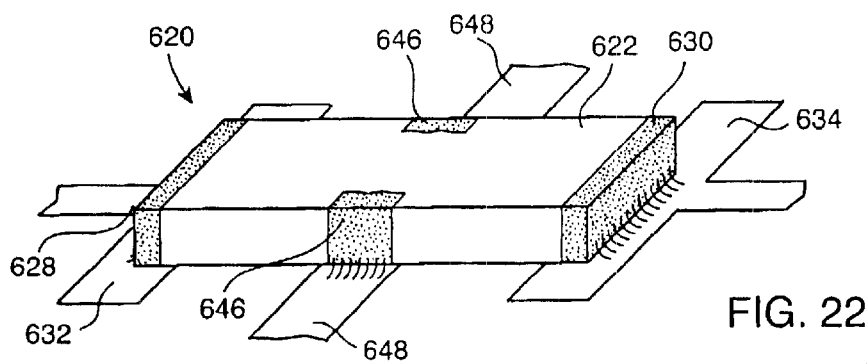
FIG. 22 is a perspective view of an integrated EMI filter-DC blocking capacitor embodying the present invention.

As shown in the drawings for purposes of illustration, the present invention is concerned with an integrated electromagnetic interference (EMI) filter-DC blocking capacitor, such as that shown in FIG. 22 and indicated by the reference number 620. As was the case previously, similar components of the various capacitors illustrated herein shall be referred to by the same reference numbers in increments of 100.

Figure 23:
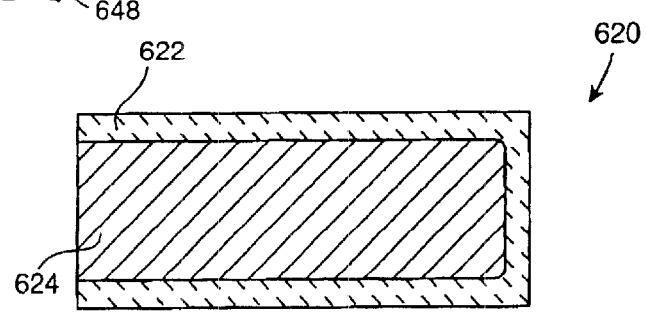
FIG. 23 is an exemplary horizontal section taken through the integrated EMI filter-DC blocking capacitor of FIG. 22, illustrating the configuration of a first set of electrode plates.
Figure 24:
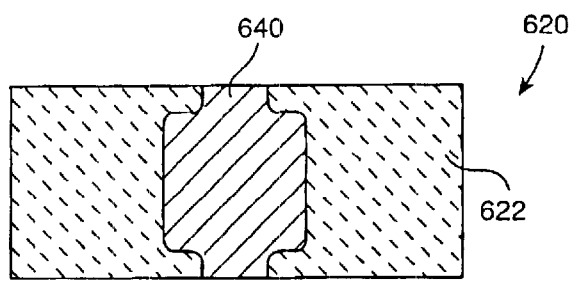
FIG. 24 is a horizontal section similar to FIG. 23, illustrating the configuration of a set of ground electrode plates.

Referring to FIGS. 22–26, the integrated capacitor 620 includes a monolithic casing of a ceramic dielectric 622 that has disposed therein alternating lay-up patterns for a first set of electrode plates 624 and a second set of electrode plates 626 separated by the ceramic dielectric 622. The first set of electrode plates 624 terminates in a first metallization band 628 exposed at one end of the integrated capacitor 620, and the second set of electrode plates 626 is conductively coupled to a second metallization band 630 disposed at an opposite end of the integrated capacitor 620. The metallization bands 628 and 630 are soldered or otherwise conductively coupled to pads for circuit traces 632 and 634. As shown in FIG. 24, ground electrode plates 640 are disposed within the monolithic casing 622 and between selected portions of the first and second sets of electrode plates 624 and 626 to form an electromagnetic interference (EMI) filter within the integrated capacitor 620. The ground electrode plates 640 terminate in two sections of a third metallization band 646 which is soldered or otherwise conductively coupled to a ground circuit trace 648. It is important that the ground electrode 640 does not completely overlap electrodes 624 and 626 as that would eliminate the series DC blocking capacitor.

Figure 11:
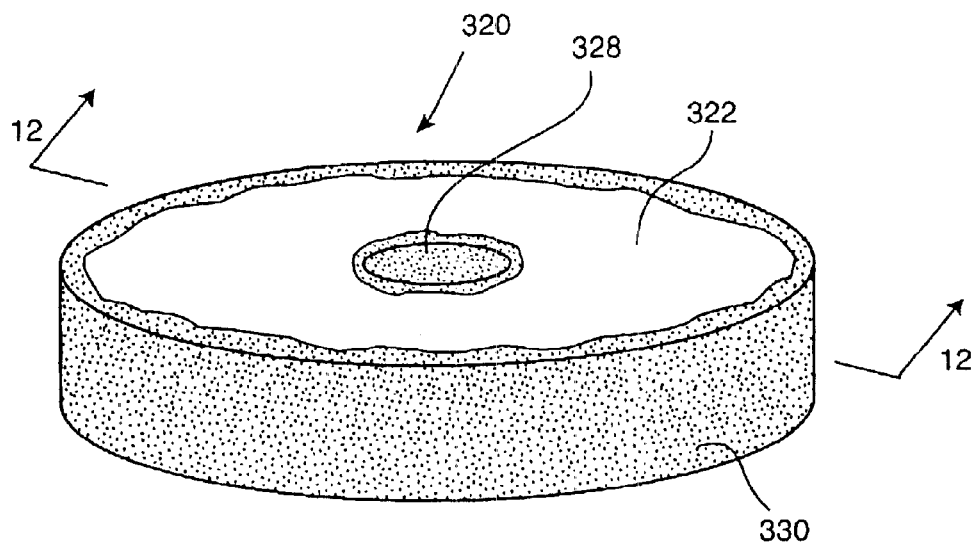
FIG. 11 is a perspective view of a single terminal prior art feedthrough capacitor.
Figure 12:
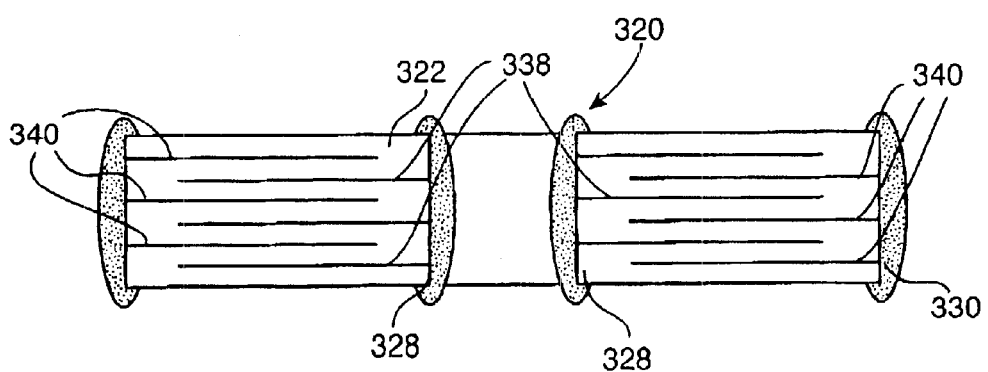
FIG. 12 is a sectional view taken generally along the line 12—12 of FIG. 11.
Figure 13:
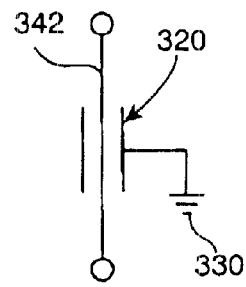
FIG. 13 is an electrical schematic diagram of the feedthrough capacitor of FIG. 11.
Figure 14:
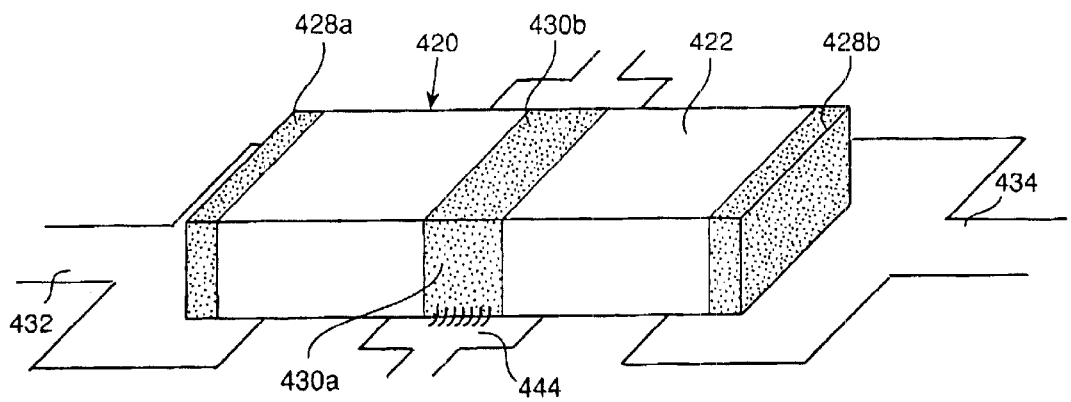
FIG. 14 is a perspective view of a prior art flat-through capacitor.
Figure 15:
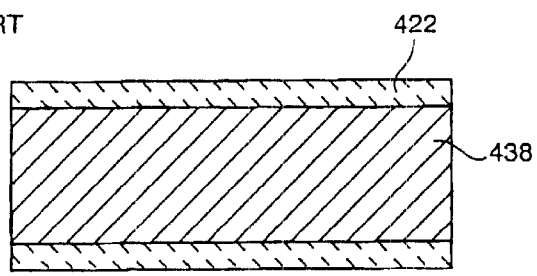
FIG. 15 is an exemplary horizontal section taken through the flat-through capacitor of FIG. 14, illustrating the configuration of a set of active electrode plates therein.
Figure 16:
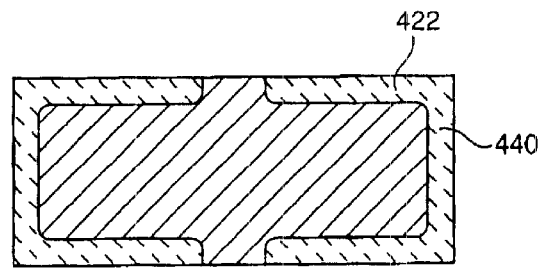
FIG. 16 is a horizontal section similar to FIG. 15, illustrating the configuration of a set of ground electrode plates therein.
Figure 17:
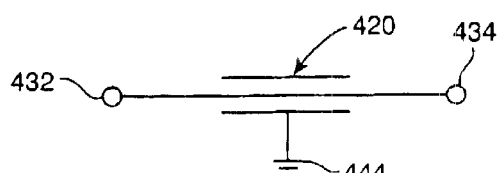
FIG. 17 is an electrical schematic diagram of the flat-through capacitor of FIG. 14.
Figure 18:
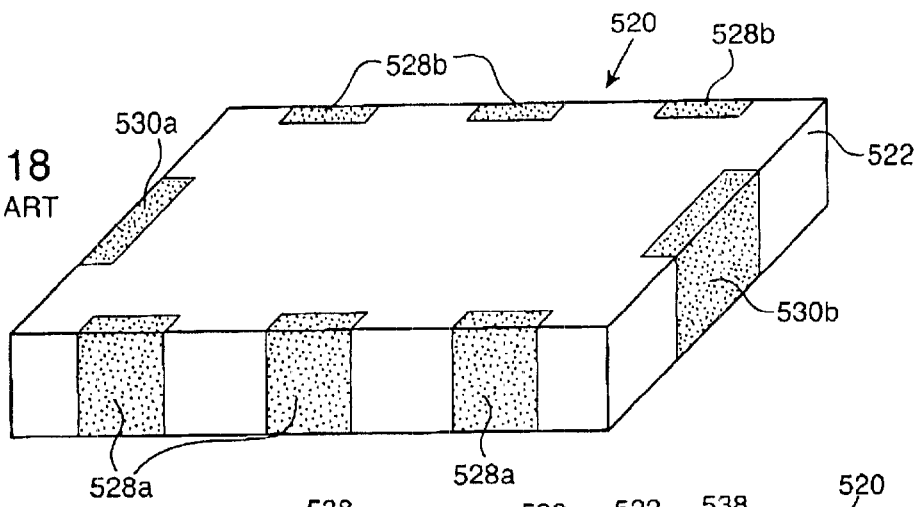
FIG. 18 is a perspective view of a prior art integrated flat-through capacitor wherein three individual capacitors are incorporated into a single monolithic package.
Figure 19:
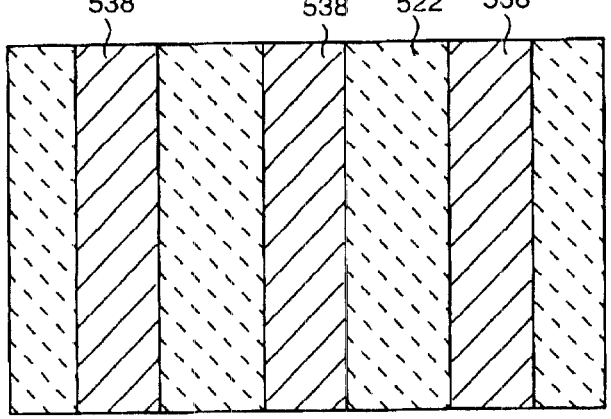
FIG. 19 is an exemplary horizontal section taken through the integrated flat-through capacitor of FIG. 18, illustrating the configuration of three distinct sets of active electrode plates therein.
Figure 20:
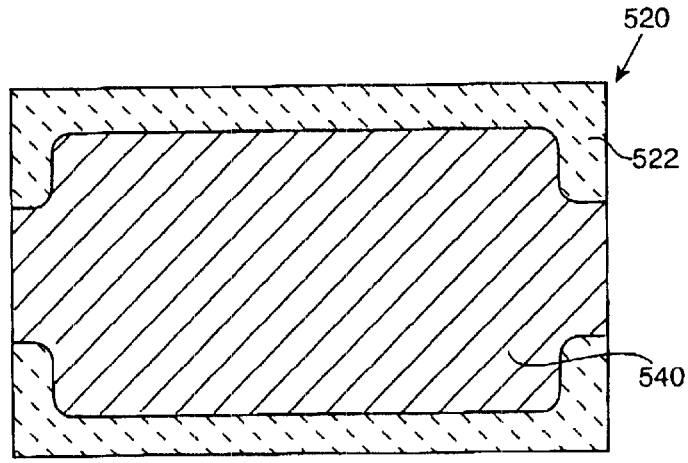
FIG. 20 is a horizontal section similar to FIG. 19, illustrating the configuration of a set of ground electrode plates.
Figure 21:
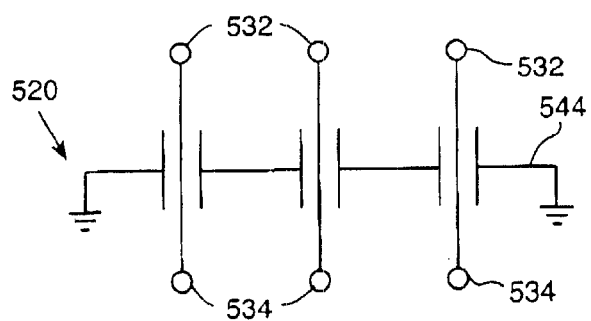
FIG. 21 is an electrical schematic diagram of the integrated flat-through capacitor of FIG. 18.
Figure 25:
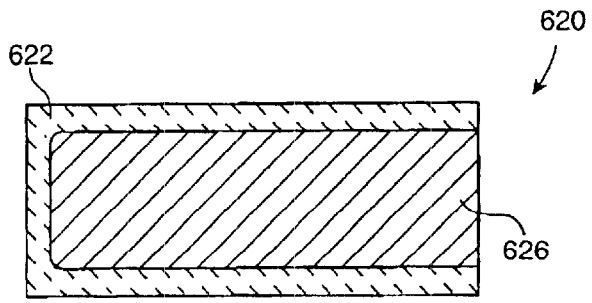
FIG. 25 is a horizontal section similar to FIG. 23, illustrating the configuration of a second set of electrode plates.

As can be seen, the capacitor of FIG. 22 has right and left terminations 628, 630 similar to the "flat-thru" capacitor as described in FIG. 14. FIG. 22 also has ground electrode metallization 646, which is also in some ways similar to the "flat-thru" capacitor. FIG. 23 is the left hand electrode plate set 624. This is substantially different than a "flat-thru" capacitor in that the electrode of FIG. 23 does not go all the way through the capacitor. FIG. 23 is interleaved between the ground electrode plates 640 of FIG. 24. FIG. 25 is the right hand electrode plate set 626 of FIG. 22. Capacitance is formed between the electrode plates 624 and 626 forming a conventional DC blocking or series capacitor. At the same time, "flat-thru" type feedthrough capacitor performance is achieved by the capacitance formed between electrode plates 624 and ground electrode plates 640, and also from electrode plates 626 and ground electrode plates 640.

Figure 26:
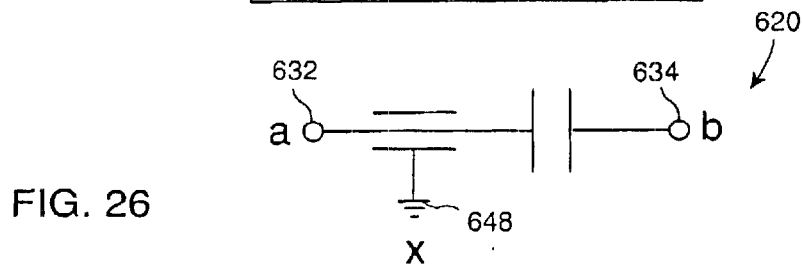
FIG. 26 is an electrical schematic diagram for the integrated EMI filter-DC blocking capacitor of FIG. 22.
Figure 27:
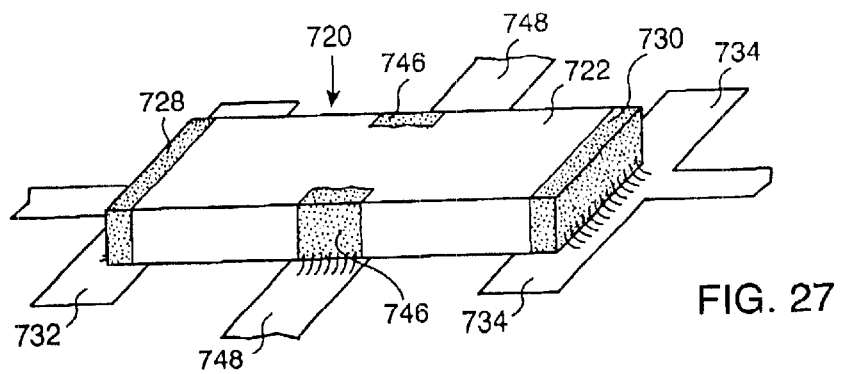
FIG. 27 is a perspective view similar to FIG. 22 of an integrated EMI filter-DC blocking capacitor embodying the present invention, wherein a base metal electrode bearing nickel is utilized to introduce inductance therethrough.

FIG. 26 is the schematic diagram of the novel integrated DC blocking- integrated EMI filter capacitor 620 of FIG. 22. As can be seen, there is a series capacitance and also a feedthrough capacitance to ground. Accordingly, the capacitor 620 of FIG. 22 effectively decouples or blocks DC signals through the device while at the same time attenuates undesirable high frequency EMI signals. It is preferable that the integrated capacitor 620 of FIG. 22 be mounted in close proximity to the ingress and egress of lead wires of the overall electromagnetic shield of an electronic device. For example, in a cardiac pacemaker or an implantable defibrillator it would be desirable to have the capacitor 620 of FIG. 22 mounted very close to the hermetic seal where the lead wires penetrate and enter into body fluids and tissues. The ground electrode connection to ground electrode plate set 640 must be of a very high integrity and there must be a continuous ground plane for the capacitor to work effectively at very high frequencies.

Over the last several years there has been a great deal of development work in order to reduce the cost of the electrodes typically used in monolithic ceramic capacitors. This is true for both monolithic ceramic capacitor chips and also for feedthrough capacitors. The most common approach is to use a base metal electrode system primarily composed of nickel. A number of manufacturers have developed nickel electrodes which replace the precious metal electrodes that have been in common use. Typical prior art electrodes include palladium, palladium silver, platinum and ternary (gold-platinum-palladium). A disadvantage of the nickel electrode in these prior art applications is that it tends to have higher inductance as compared with the noble metal electrodes. It is a unique feature of the integrated DC blocking-EMI filter that this inductance can be helpful in improving the high frequency performance of the device. This is best illustrated in FIGS. 27–31.

FIGS. 27–31 illustrate an alternative embodiment of the integrated capacitor 720 of the present invention. In all respects, with the exceptions noted below, the construction of the integrated capacitor 720 is the same as that illustrated and described in connection with the integrated capacitor 620 of FIG. 22.

Figure 28:
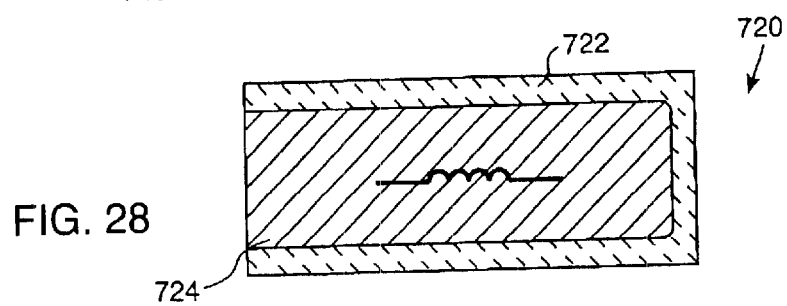
FIG. 28 is an exemplary horizontal section taken through the integrated EMI filter-DC blocking capacitor of FIG. 27, illustrating the configuration of a first set of electrode plates therein.
Figure 29:
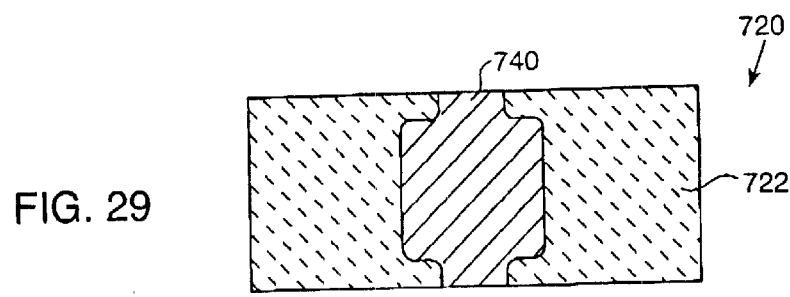
FIG. 29 is a horizontal section similar to FIG. 28, illustrating the configuration of a set of ground electrode plates.
Figure 30:
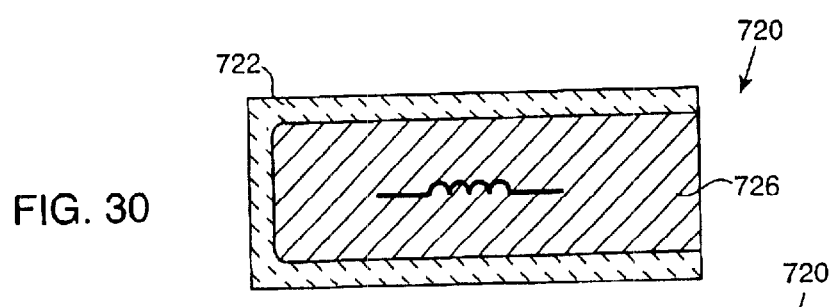
FIG. 30 is a horizontal section similar to FIG. 28, illustrating the configuration of a second set of electrode plates.
Figure 31:
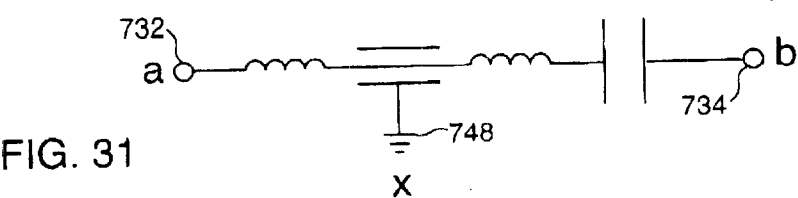
FIG. 31 is an electrical schematic diagram of the integrated EMI filter-DC blocking capacitor of FIG. 27.

FIG. 28 shows the left hand DC blocking electrode plate 724 which would have an increased inductance as shown in the figure if a base metal electrode bearing nickel is used. Accordingly the corresponding right hand electrode plate 726 as shown in FIG. 30 would also have an increased inductance. This can best described as shown in FIG. 31 which is the electrical schematic of the capacitor 720. As can be seen, series inductance has been added which improves the effect of the high frequency filtering capacitor to ground. This effectively makes this element into a very effective T filter or L filter. For implantable medical device applications this small series inductance has very little effect on the ability of the device to desirably couple, for example, cardiac signals. However, the small inductance becomes quite significant at high frequency such as cellular telephone frequencies. Cellular telephones typically work in the range of approximately one gigahertz. This small inductance does have a very high inductive reactance at that frequency. This effectively raises the series impedance at cellular telephone frequencies. At the same time the capacitor to ground has very low impedance at these frequencies. When working in combination, the series inductance and the capacitance to ground forms what's known in the art as a very effective T filter. Because of this, much higher at tenuation at levels at cellular telephone frequencies are achieved.

Figure 32:
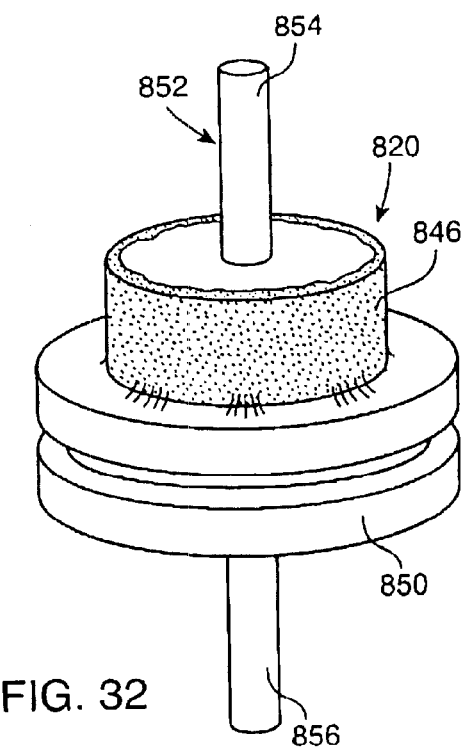
FIG. 32 is a perspective view of another type of integrated EMI filter/DC blocking capacitor embodying the invention.
Figure 33:
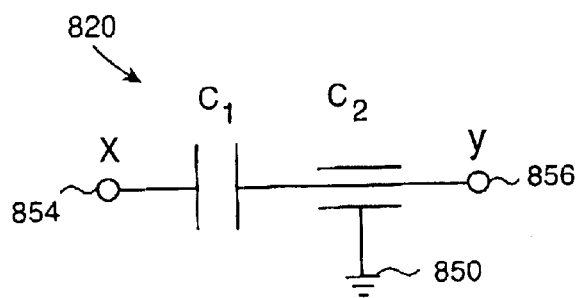
FIG. 33 is an electrical schematic diagram of the integrated capacitor of FIG. 32.

FIGS. 32–38 illustrate yet another embodiment of a unipolar feedthrough-style, integrated DC blocking capacitor and EMI filter 820 which is conductively coupled to an underlying ferrule 850 and through which a discontinuous lead wire 852 extends in non-conductive relation with the ferrule 850. FIG. 33 is the schematic diagram of the integrated capacitor 820 of FIG. 32. The capacitor 820 of FIG. 32 is shown mounted to a hermetic terminal or ferrule 850 suitable for installation into a cardiac pacemaker or the like.

Figure 34:
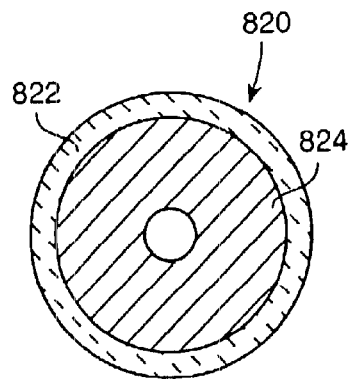
FIG. 34 is an exemplary horizontal section taken through the integrated capacitor of FIG. 32, illustrating the configuration of a first set of electrode plates therein.
Figure 35:
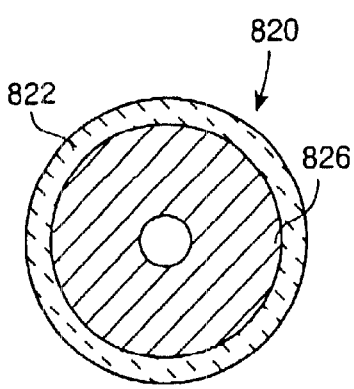
FIG. 35 is a horizontal section similar to FIG. 34, illustrating the configuration of a second set of electrode plates.
Figure 36:
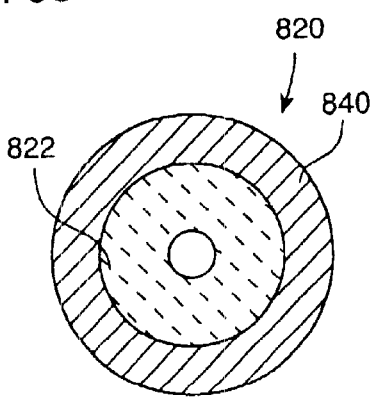
FIG. 36 is a horizontal section similar to FIGS. 34 and 35, illustrating the configuration of a set of ground electrode plates.

FIG. 34 illustrates one electrode plate set 824 which would be, for example, connected to an uppermost segment 854 of the lead wire 852, and FIG. 35 is another active plate set 826, which would connect to, in this case, the bottom lead segment 856 of the lead wire 852. FIG. 36 is the ground electrode plate set 840 which communicates between plate sets 824 and 826.

Figure 37:
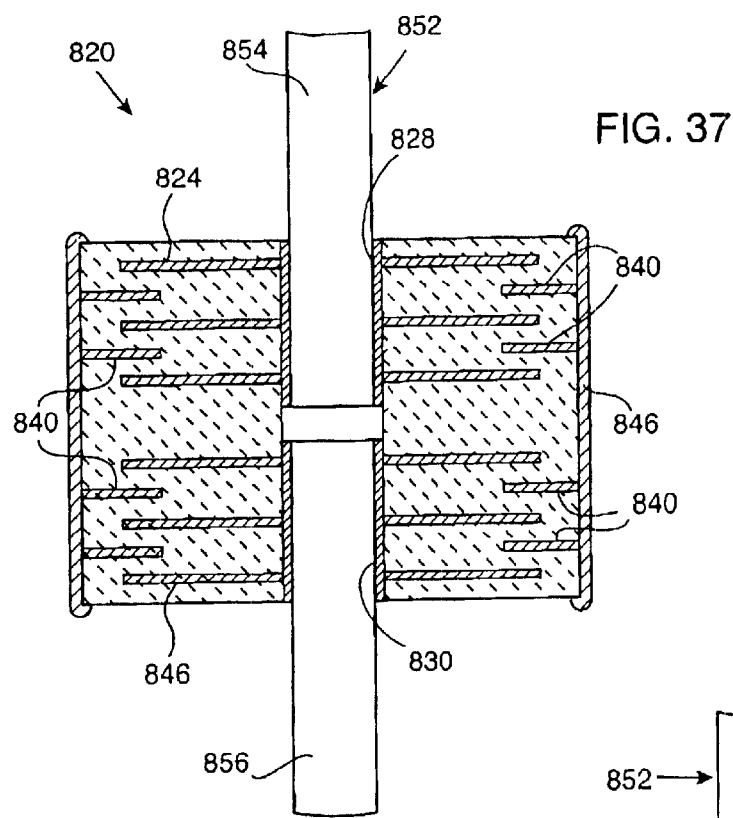
FIG. 37 is an enlarged vertical section of the integrated capacitor of FIG. 32, wherein a lead wire is discontinuous within the capacitor.

FIG. 37 is a cross sectional drawing of the capacitor of FIG. 32. As can be seen, the lead wire 852 is discontinuous in that it does not run all the way through the capacitor 820. It can also be seen that the inside diameter metallization 828, 830 is also discontinuous in that it does not run all the way through the capacitor.

Figure 38:
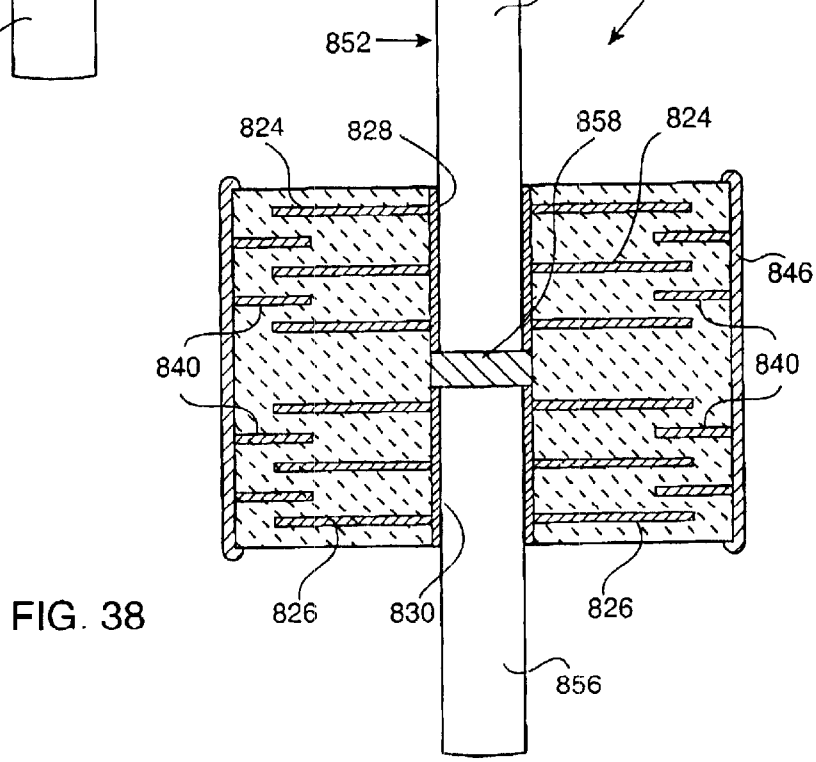
FIG. 38 is an enlarged sectional view similar to FIG. 37, wherein an insulative spacer is added between abutting ends of two lead wire segments.

FIG. 38 is a cross sectional drawing which is very similar to the capacitor 820 of FIG. 37, except that an insulative spacer 858 has been added between the two lead wire segments 854 and 856 to make sure that they are reliably separated. The spacer 858 can be manufactured of alumina ceramic, plastics, epoxies, polyamides or any other insulative material suitable for providing a defined gap to insure that the two lead wire segments are electrically and mechanically isolated.

FIGS. 39–44 illustrate a novel quad polar integrated DC blocking-EMI filter capacitor 920 shown mounted to a hermetic terminal 950 suitable for installation into a cardiac pacemaker or the like. FIG. 40 is one electrode plate set 924. These electrode plates 924 are connected to the four lead wires 954. FIG. 41 illustrates the electrode plate set 926 of the capacitor 920 of FIG. 39. As can be seen, the bottom lead wires 956 make contact and connect to the 926 electrode plates in one corner. The uppermost lead wires 954 pass through the electrode plates 926 in nonconductive relation. FIG. 42 illustrates the ground electrode plate set 940 of the capacitor 920. As can be seen, none of the active lead wires 954, 956 are connected to this ground electrode. EMI filter capacitance is formed between the ground electrodes 940 of FIG. 42 and the active electrodes 924 and 926 of FIG. 40 and FIG. 41.

FIG. 43 is a cross sectional drawing of the capacitor 920 of FIG. 39. As can be seen, DC blocking capacitance is formed between the active electrodes 924 and 926 as they overlap. In addition, a "feed through" EMI filter capacitance is formed between the ground electrode plates 940 and both active electrode plate sets 924 and 926. This is best illustrated in the schematic drawing of FIG. 44, wherein one can see four DC blocking capacitors in series with four EMI feedthrough capacitors. An alternative to the cross section as shown in FIG. 43, is to have the feedthrough holes run all the way through the capacitor instead of bottomed as presently shown. In the case where they run all the way through, the lead wire 952 would stop short and a small dollop of epoxy or other suitable material would be placed on top of the exposed lead in order to cover up the hole. In capacitor manufacturing, it is easier to run the holes all the way through and then use an epoxy, polyamide or similar insulating material to cover the lead tip. This principle will be shown in subsequent figures.

Figure 45:
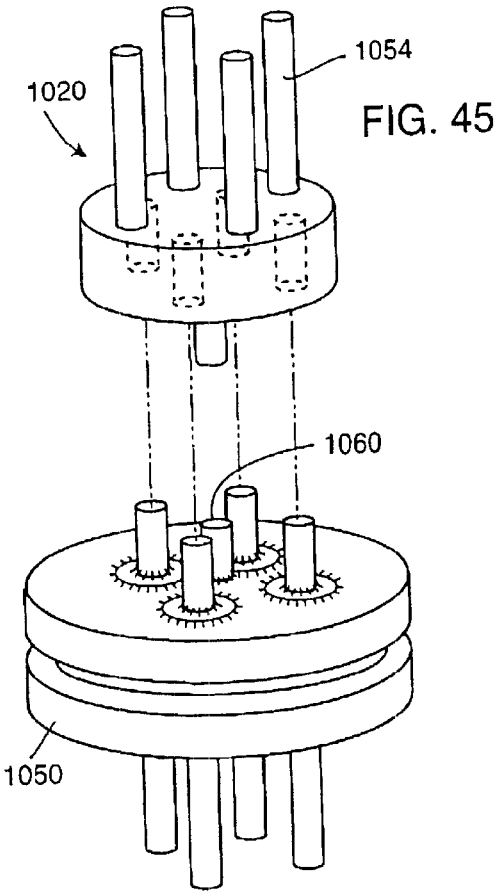
FIG. 45 is an exploded perspective view of an internally grounded version of the quad polar integrated DC blocking-EMI filter capacitor of FIG. 39.
Figure 46:
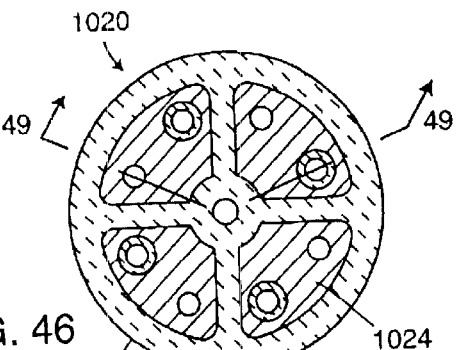
FIG. 46 is an exemplary horizontal section taken through the internally grounded quad polar capacitor of FIG. 45, illustrating the configuration of a first set of electrode plates therein.
Figure 47:
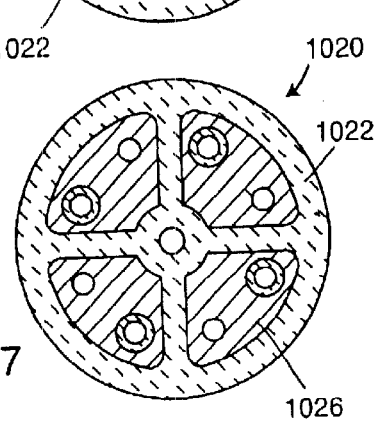
FIG. 47 is a horizontal section similar to FIG. 46, illustrating the configuration of a second set of electrode plates.
Figure 48:
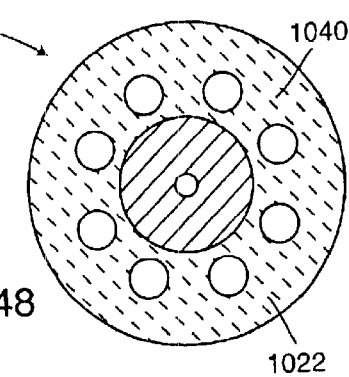
FIG. 48 is a horizontal section similar to FIGS. 46 and 47, illustrating the configuration of a set of ground plates.

FIGS. 45–49 illustrate an internally grounded version 1020 of the quad polar integrated DC blocking—EMI filter capacitor 920, of FIG. 39. FIG. 46 illustrates one active electrode plate set 1024, and FIG. 47 illustrates the other (offset) electrode plate set 1026. FIG. 48 illustrates an internally grounded electrode plate set 1040, which is connected to a grounded center pin 1060. It will be noted that the center pin 1060 is welded or otherwise conductively attached as an integral part of the conductive ferrule 1050 of the hermetic seal and thus is effectively grounded.

Figure 49:
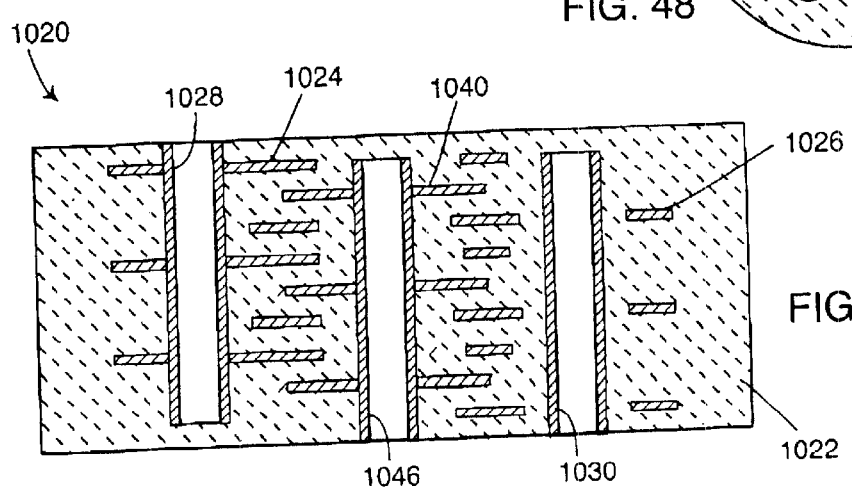
FIG. 49 is an enlarged sectional view taken generally along the lines 49—49 of FIG. 46.

FIG. 49 is a cross sectional view of the internally grounded integrated DC blocking—EMI quad polar filter capacitor 1020 of FIG. 45. As can be seen, DC blocking or series capacitance is formed between the active electrode plate sets 1024 and 1026. EMI filter capacitance (feedthrough capacitance) is formed between the overlapped areas of the ground electrode plate set 1040 and the active electrode plate sets 1024 and 1026. The schematic diagram for the integrated capacitor 1020 of FIG. 45 is exactly the same as shown in FIG. 44.

Figure 50:
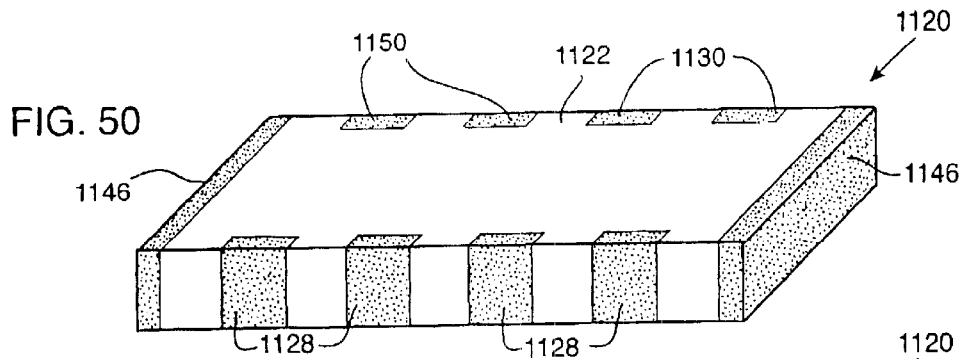
FIG. 50 is a perspective view of a quad polar flat-through integrated DC blocking-EMI filter capacitor.
Figure 51:
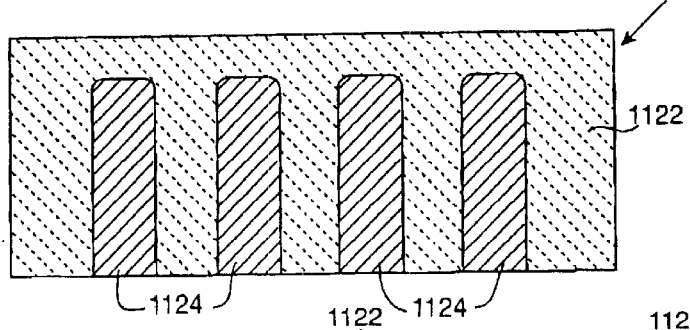
FIG. 51 is an exemplary horizontal section taken through the quad polar flat-through integrated DC blocking-EMI filter capacitor of FIG. 50, illustrating the configuration of four distinct first sets of electrode plates therein.
Figure 52:
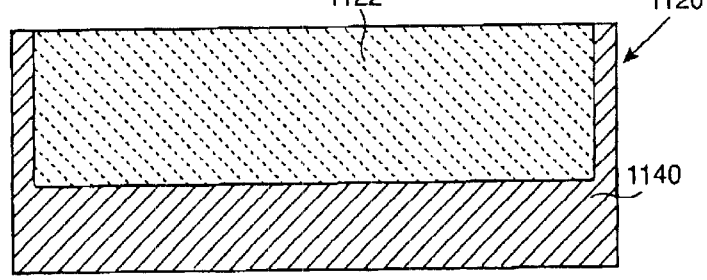
FIG. 52 is a horizontal section similar FIG. 51, illustrating the configuration of a set of ground plates therein.
Figure 53:
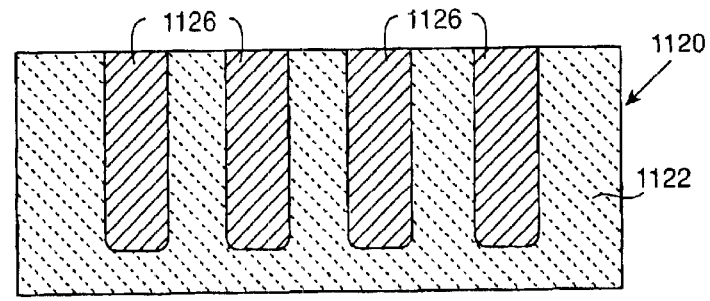
FIG. 53 is a horizontal section similar to FIGS. 51 and 52, illustrating the configuration of four distinct second sets of electrode plates.

FIGS. 50–54 illustrate a quad polar Flat Thru integrated DC blocking—EMI filter capacitor 1120. FIG. 51 shows one active electrode plate set 1124, FIG. 52 shows a ground electrode plate set 1140, and FIG. 53 shows the other electrode plate set 1126. DC blocking capacitance is formed between electrode plate sets 1124 and 1126. The ground electrode plate set 1140 overlaps partially both the electrodes sets 1124 and 1126. It is important that the ground electrodes 1140 do not completely overlap the DC blocking electrode plate sets 1124 and 1126 in any of the designs. If the ground electrode 1140 were to completely overlap these plates, there would be no DC blocking capacitance. This is because the ground electrode plate would effectively shield the active electrodes from one another. This is true in any of the integrated DC blocking—EMI filter capacitors as illustrated herein.

Figure 54:
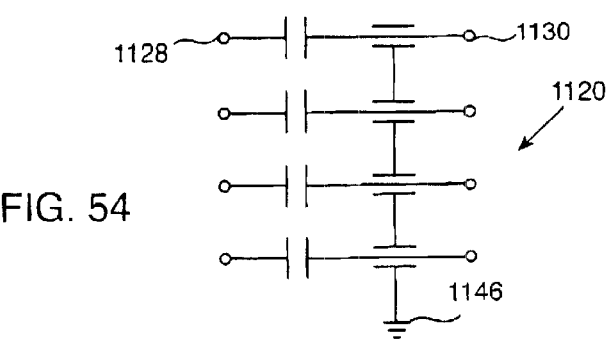
FIG. 54 is an electrical schematic diagram of the quad polar flat-through integrated DC blocking-EMI filter capacitor of FIG. 50.

FIG. 54 is the schematic diagram of the rectangular integrated DC blocking capacitor—EMI filter 1120 of FIG. 50.

Figure 55:
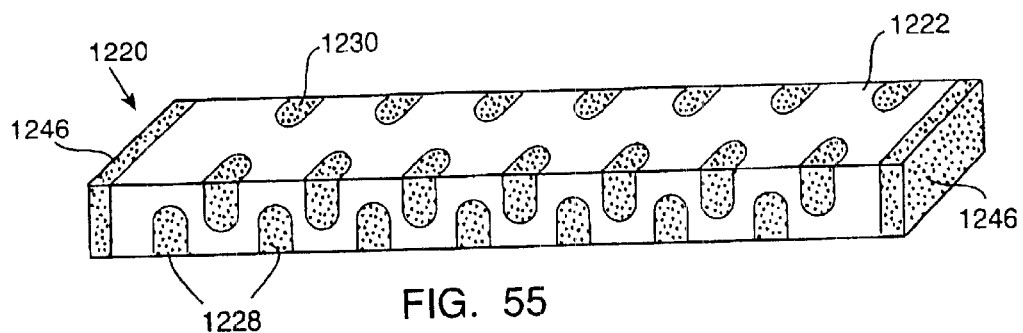
FIG. 55 is a perspective view of yet another embodiment of a novel integrated DC blocking-EMI filter capacitor.
Figure 56:
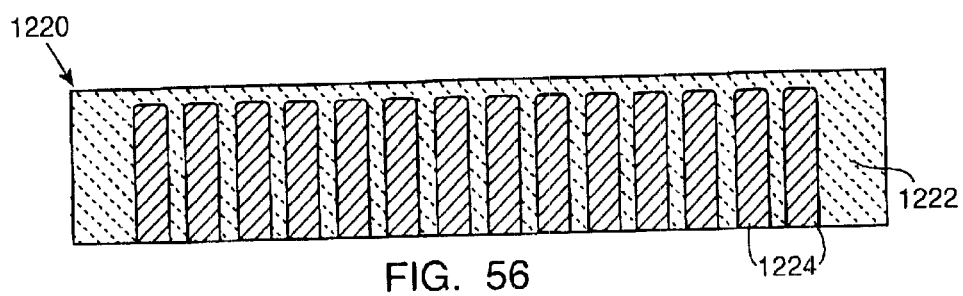
FIG. 56 is an exemplary horizontal section taken through the integrated capacitor of FIG. 55, illustrating the configuration of fourteen distinct first sets of electrode plates therein.
Figure 57:
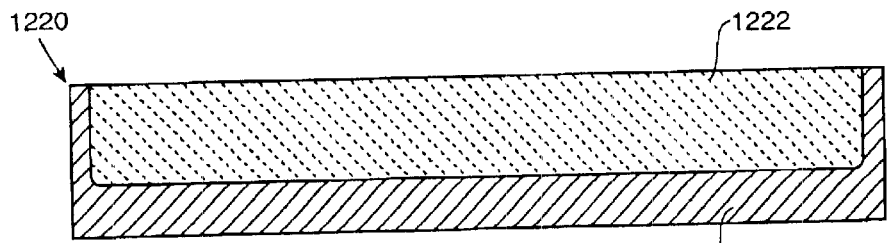
FIG. 57 is a horizontal section similar to FIG. 56, illustrating the configuration of a set of ground electrode plates.
Figure 58:
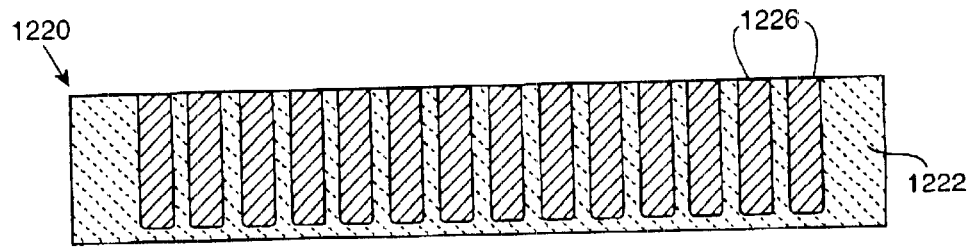
FIG. 58 is a horizontal section similar to FIGS. 56 and 57, illustrating the configuration of fourteen distinct second sets of electrode plates.
Figure 59:
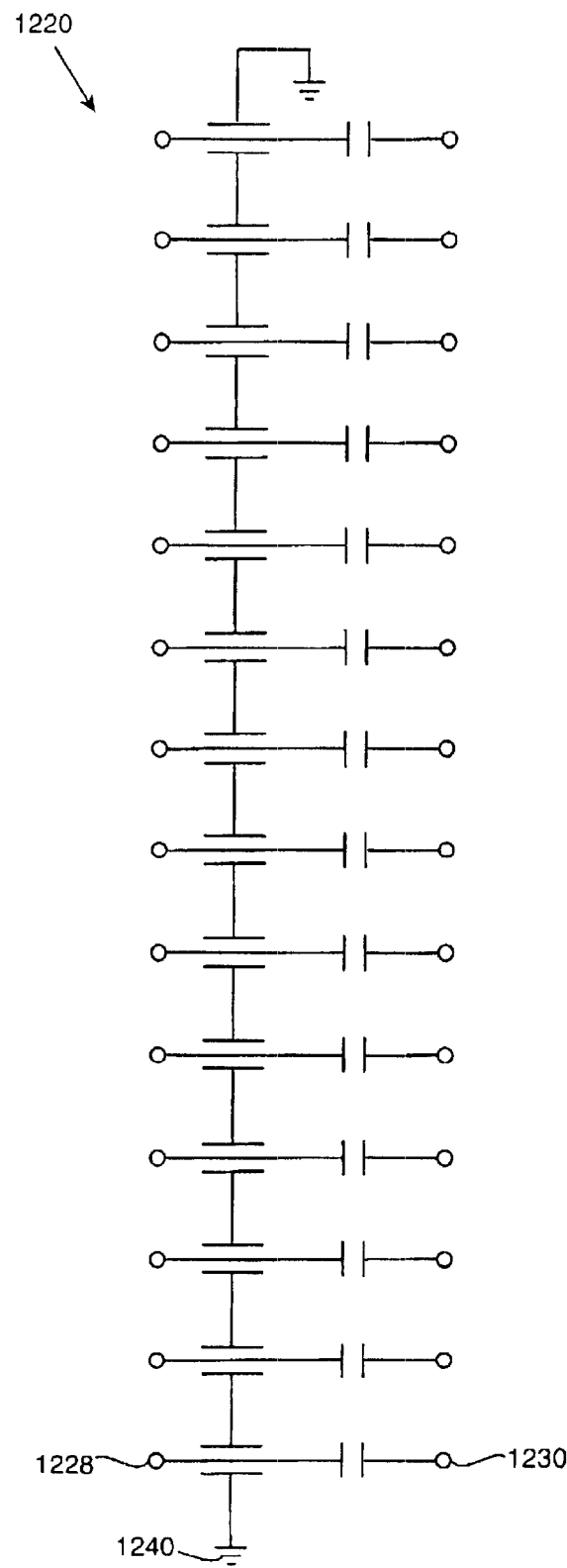
FIG. 59 is an electrical schematic diagram showing the fourteen integrated DC blocking/EMI filter capacitors within the integrated capacitor of FIG. 55.

FIGS. 55–59 illustrate yet another embodiment of an novel integrated DC blocking—EMI filter capacitor 1220. FIG. 55 shows the isometric view of this 14-terminal pad (on each side) device 1220. FIG. 56 shows one active electrode plate set 1224 of the capacitor 1220. As can be seen, there are fourteen active electrodes. FIG. 57 is the ground electrode plate set 1240. FIG. 58 is the opposite set of active electrodes 1226. FIG. 59 is a schematic diagram showing the fourteen distinct integrated DC blocking—EMI filter capacitors of FIG. 55. As can be seen, there are both DC blocking capacitors in series in each circuit, as well as, EMI filter feedthrough capacitors. The series DC blocking capacitor is created by the overlap of the areas of the active electrodes 1224 as shown in FIG. 56 with the active electrodes 1226 as shown in FIGS. 58. The EMI filter capacitor to ground is created by the overlap of the ground electrode plate set 1240 with the active electrode plate sets 1224 and 1226.

Figures 60, 61:
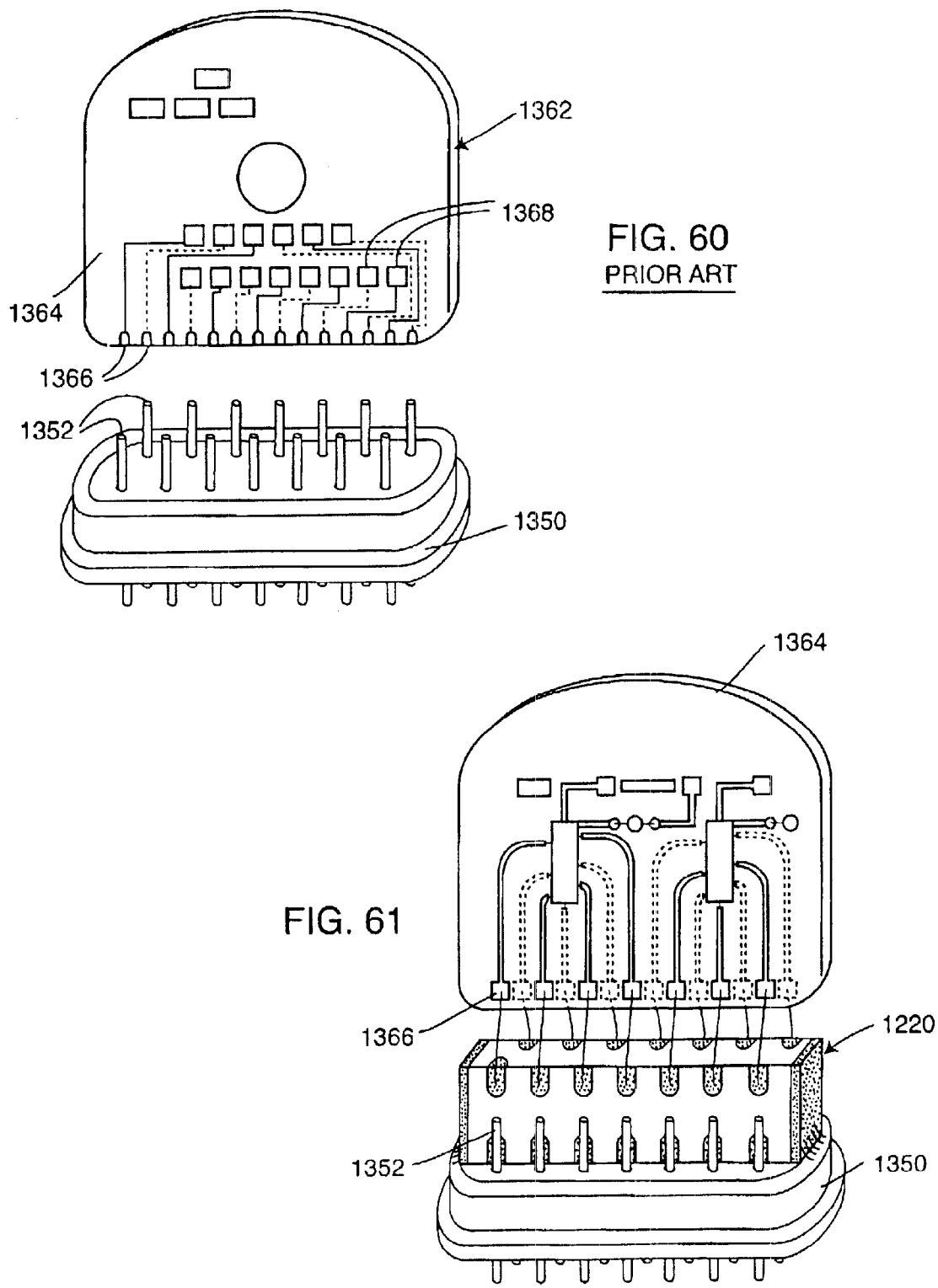
FIG. 60 is an exploded perspective view of a prior art medical device such as cochlear implant.
FIG. 61 is a perspective view similar to FIG. 60, with the addition of a fourteen pin integrated DC blocking/EMI filter capacitor such as that shown in FIG. 55.

FIG. 60 is an isometric drawing of a typical medical device such as a cochlear implant 1362. At the bottom of FIG. 60, is a hermetic seal 1350 with fourteen terminal pins 1352. Typically the hermetic terminal 1350 consists of an outer flange or ferrule. The fourteen terminal pins 1352 are held in non-conductive or insulative relationship by means of a hermetic seal formed of either sealing glass or alumina ceramic. The hermetic seal can be formed in a variety of ways, which are already well known in the art, such as glass compression sealing, glass fusion sealing, gold brazing to alumina, or other techniques. As these methods are already well known in the art, there will be no further discussion herein. The substrate 1364 shown in the upper half of FIG. 60 is conveniently sandwiched in between the terminal pins 1352 and electrical connections are made from each pin to the circuit board lands 1366 as shown. These lands are spaced such that they will lay out on the terminal pins. An electrical and mechanical connection is then made from each terminal pin to the land on the circuit board. This can be done by solder, thermal setting conductive adhesives, or various types of welding operations. FIG. 60 shows prior art DC blocking capacitors 1368 mounted on the substrate. There are no three-terminal EMI filter capacitors.

FIG. 61 is basically the same arrangement as FIG. 60, except that the fourteen pin integrated DC blocking—EMI filter capacitor 1220 of FIG. 55 is added. Because the DC blocking capacitors are integrated into the EMI filter, the fourteen discrete DC blocking capacitors are eliminated from the circuit board (see FIG. 60). Elimination of these fourteen blocking capacitors 1368 saves a significant amount of space on the circuit board. In FIG. 61, connection between each individual pin 1352 and the capacitor 1220 is affected in the same manner as previously described in FIG. 60 using either solder, conductive adhesives or welding/brazing operations. It is essential (as shown in FIG. 61), that both ends of the integrated capacitor 1220 be electrically connected with solder, conductive adhesive, or the like shown in FIG. 61 to the titanium ferrule 1350 such that an RF ground is formed to the ground electrode plates 1240 of the capacitor 1220. This is important so that the feedthrough capacitor portion can operate effectively at high frequencies.

In order to make the integrated DC blocking—EMI filter capacitor small in size for human implant applications, it would be desirable to have a ceramic dielectric formulated of much higher dielectric (k) material than is presently used in the art. Such is also important in view of recently imposed stringent standards and requirements for the Electromagnetic Compatibility (EMC) of implantable medical devices (ref.AAMI PC69) Accordingly, there is a need for such a high k dielectric which is optimized for operation at body temperature (37 degrees C.). As one increases the k of ceramic dielectrics (typically barium titanate based), the temperature and DC voltage stability are both compromised. That is, as the operating temperature is raised or lowered, for example to +125 or −55 degrees C., there would be a very significant drop in capacitance. The NPO, BX and X7R dielectrics used in prior art human implant DC blocking capacitors and EMI filters typically vary in capacitance by plus or minus 15% over these temperature extremes (these dielectrics and temperature characteristics come from EIA standards and military applications/space high reliability applications where operation over large temperature ranges is required). The design curie point of these stable dielectric formulations is typically set at +125 degrees C. which is usually the upper end of temperature performance. It is preferred that the curie point be placed between 10 and 55 degrees C. in order to optimize the dielectric constant for human implant applications only (body temperature is 37 degrees C.). By moving the curie point to 37 degrees C. (by modification of ceramic crystal and grain boundary dopants), the capacitor k is peaked or optimized for operation near 37 degrees C. only. This means that at 37 degrees C., the k can be increased to the range of 8500 to 22,000 as compared to the prior NPO, BX and X7R dielectrics which typically range in k from 60 to 2500. This k increase yields a dramatic reduction in the size of the capacitor and also the cost. For example, size reductions in an EMI feedthrough capacitor of two or even nine to one are realized. Cost is also reduced because fewer active layers and electrodes are required for a given capacitance value which means less labor and precious metal is used. The tradeoff is that the capacitance will drop dramatically at temperatures outside of the 10 to 55 degree C. range. However, this does not matter for a human implant application since the filter capacitor(s) is only subjected to a single operating temperature, which is 37 degree C.

The use of these very high k materials which are optimized for 37 degree C. operation will also allow for more capacitance per unit volume. This is particularly important in the next generation implantable EMI feedthrough filters, which must now provide effective attenuation at lower frequencies. This is due to the increasing EMI threat of Electronic Article Surveillance Systems (EAS or retail store security systems), security scanners, Radio Frequency Identification (RFID) systems and the 27 MHz and 70/76 MHz hobbyist operating bands for model airplanes, boats, helicopters and the like.

A previously thought to be undesirable property of extremely high k dielectrics is that the k (and therefore capacitance) does drop dramatically in the presence of DC bias voltages measured in volts per mil of dielectric thickness. However, this is not a problem at all in pacemakers, cochlear implants and neurostimulators where the therapeutic impulses are very low in magnitude (in the range of only a few volts). The large drop in capacitance in a HV implantable cardioverter defibrillator (ICD) application is actually an advantage. Having the capacitance of an EMI filter drop during the ICD pulse is an advantage as there would be less capacitive loading of the circuit during the pulse discharge, less energy loss, and less capacitor electrode plate charging current. See, for example, U.S. Pat. No. 5,978,204, the contents of which are incorporated herein. When the ICD is passive (monitoring cardiac electrical activity), the capacitance of the EMI filter would be desirably high, which is exactly the time when EMI is a concern.

Figure 62:
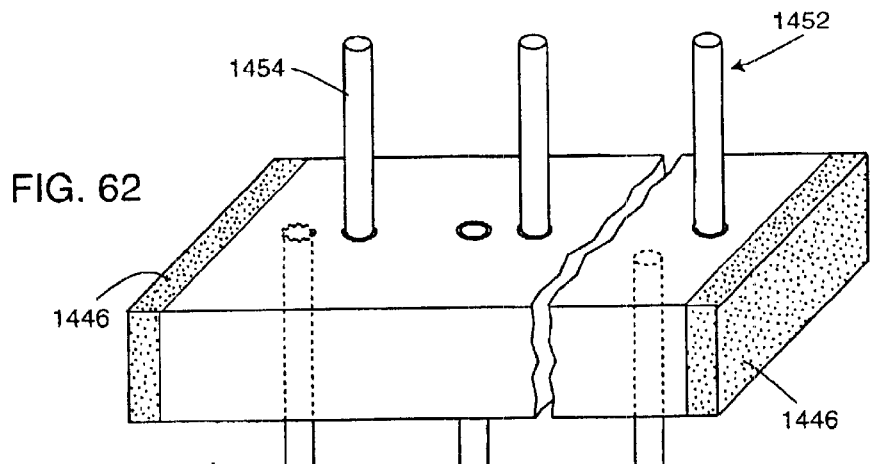
FIG. 62 is a fragmented perspective view of a rectangular integrated DC blocking-EMI filter capacitor employing three sets of inline terminal pins.
Figure 63:
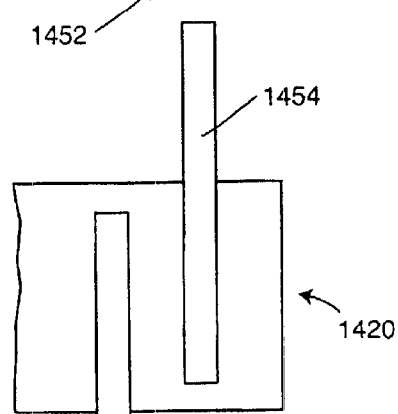
FIG. 63 is an enlarged sectional view of a portion of the capacitor of FIG. 62, wherein the monolithic casing is provided with bottomed holes.
Figure 64:
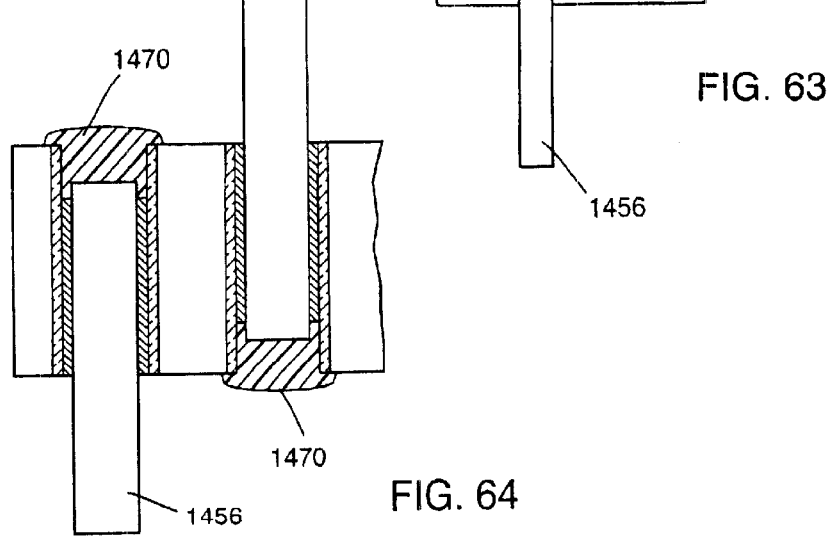
FIG. 64 is a fragmented sectional view similar to FIG. 63, illustrating another embodiment wherein the integrated capacitor of FIG. 62 is provided with through-holes for receiving the terminal pins.

FIG. 62 illustrates a rectangular integrated DC blocking—EMI filter capacitor 1420 employing three sets (tripolar) of inline terminal pins 1452. This tripolar capacitor 1420 can be manufactured with either through holes (lowest cost) as shown in FIG. 64 or with bottomed holes as shown in FIG. 63. It is a desirable option when a through hole like FIG. 64 is used, that the exposed lead tip be covered with a suitable insulative coating 1470 of epoxy or non-conductive polyamide. This coating 1470 will isolate the lead from the adjacent lead and provide additional electrical insulation against tracking, flashover or reduction in insulation resistance due to surface contamination.

FIGS. 65–67 illustrate exemplary electrode plate sets for the integrated capacitor 1420 of FIG. 62. FIG. 65 illustrates one active electrode plate set 1424, FIG. 66 is the other active electrode plate set 1426, which is offset from the electrodes shown in FIG. 65, and FIG. 67 illustrates one type of ground electrode set 1440.

FIG. 68 illustrates an alternate ground electrode 1440a, which puts the ground electrode plates down the center. The overlap area between the first and second sets of electrode plates 1424 and 1426 creates the series DC blocking capacitor. The overlap of either of the ground electrode plate sets 1440 or 1440a with the active electrodes 1424 and 1426, form the high frequency EMI filter (many other electrode configurations will be obvious to one skilled in the art).

Figure 69:
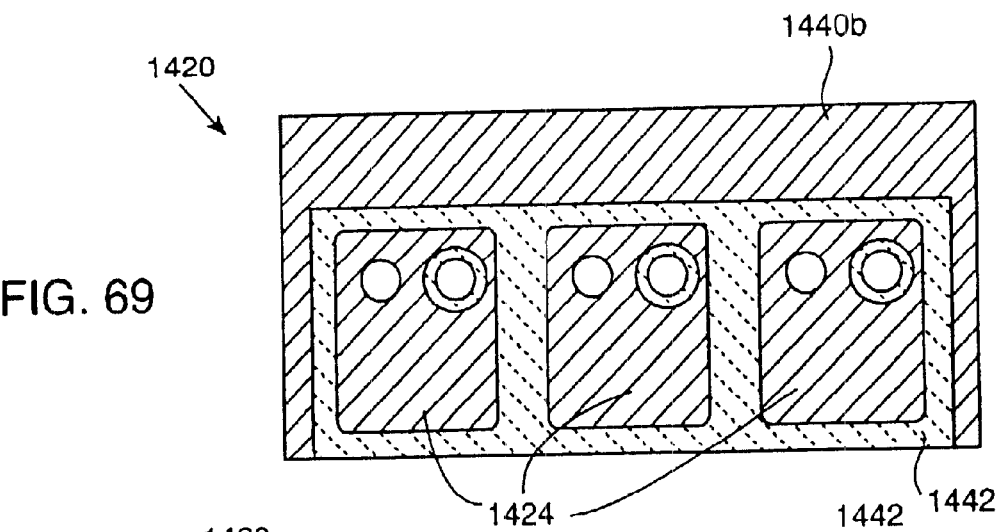
FIG. 69 is an exemplary horizontal section taken through the integrated capacitor of FIG. 62, illustrating the configuration of alternative first sets of electrode plates and ground electrode plates therein.
Figure 70:
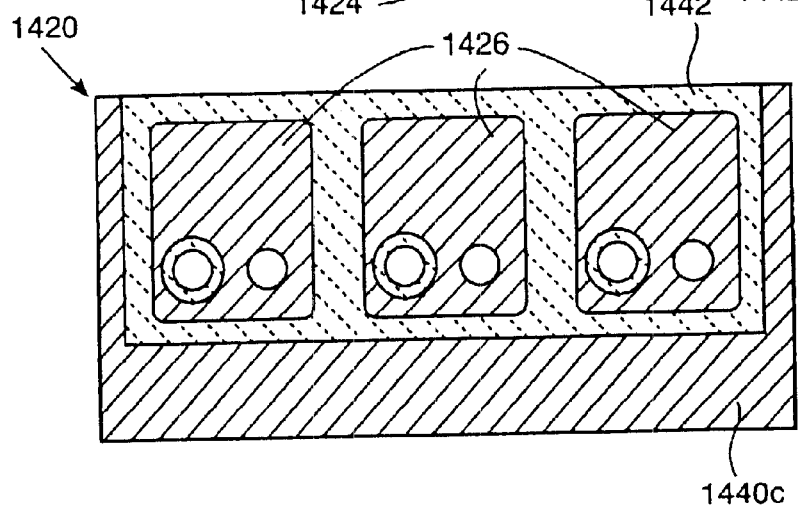
FIG. 70 is a horizontal section similar to FIG. 69, illustrating the configuration of alternative second sets of electrode plates and ground plates therein, wherein the alternative arrangement of FIGS. 69 and 76 are utilized in conjunction with one another to achieve the desired blocking and filtering characteristics.

FIGS. 69 and 70 are yet again another set of alternative electrodes for the capacitor 1420 illustrated in FIG. 62. This is the preferred embodiment in that it is easier to manufacture since there are only two different electrode screen patterns. As can be seen, FIG. 69 has an active electrode plate set 1424 and a ground electrode plate set 1440b. FIG. 70, which is a reverse image, also has the three opposite electrode plates 1426 and it also has its own ground plate 1440c. As previously described, the overlap between the two-electrode plate sets forms the DC blocking capacitor. More importantly, the partial overlap of these active electrode plates and the respective ground plate of the opposite set, forms a high frequency EMI filter.

Figure 71:
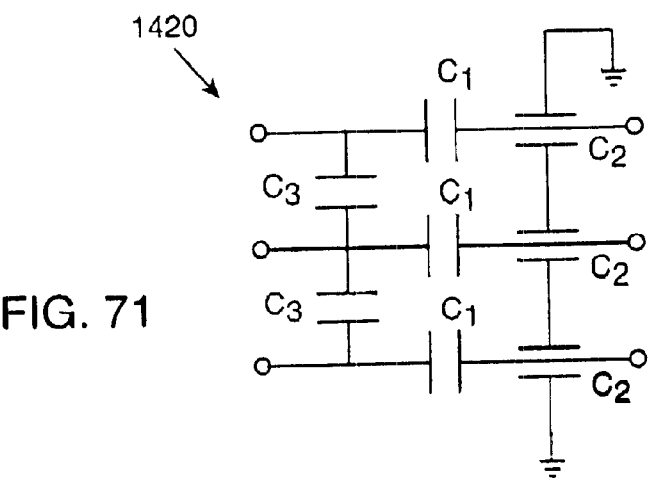
FIG. 71 is an electrical schematic diagram of the integrated capacitor of FIG. 62.

FIG. 71 illustrates the schematic diagram of the integrated capacitor of FIG. 62. The schematic in FIG. 71 illustrates the series blocking capacitors C1 and the EMI filtered capacitors C2 (feedthrough capacitors) to ground. The line-to-line capacitors C3 shown in the schematic in FIG. 71 are undesirable, which create cross-talk. This is the parasitic capacitance created between the active electrode plate sets in the high-K dielectric material. Accordingly, for the capacitor of FIG. 62, this would be used in circuitry where cross-talk is not of importance.

Figure 72:
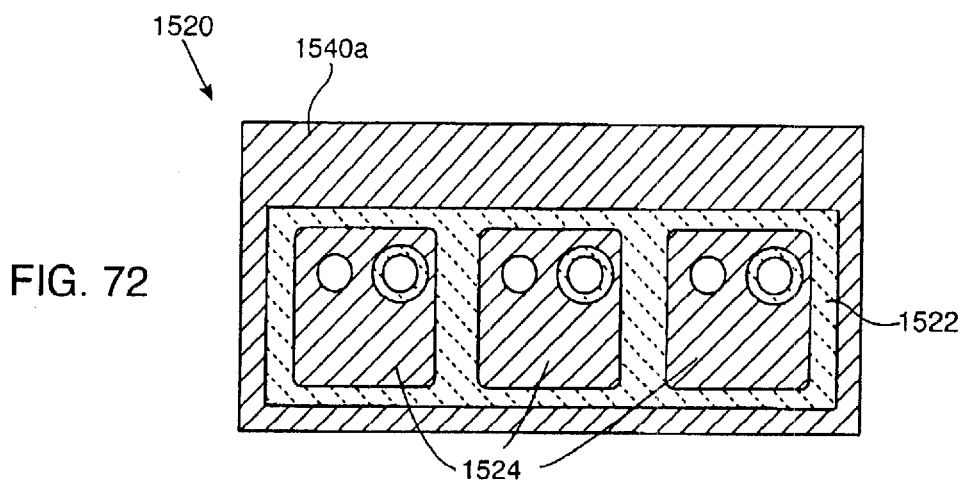
FIG. 72 is an exemplary horizontal section taken through the integrated capacitor of FIG. 62, illustrating yet another alternative configuration of first sets of electrode plates and ground electrode plates.
Figure 73:
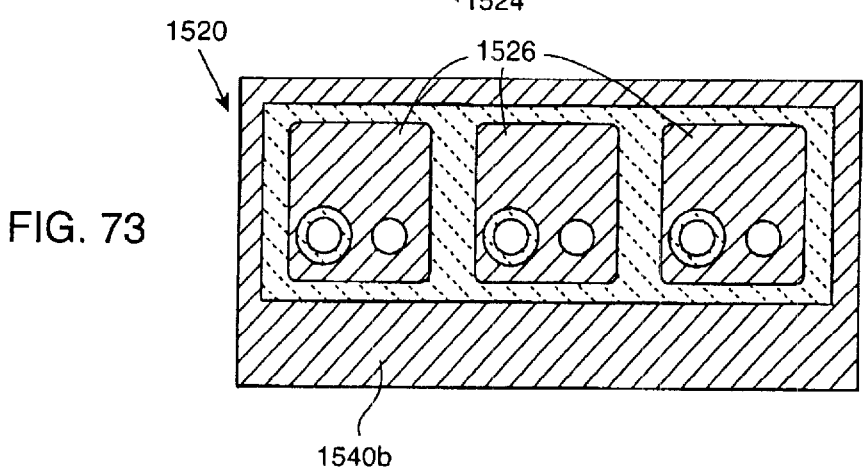
FIG. 73 is a horizontal section similar to FIG. 72, illustrating the configuration of second sets of electrode plates and corresponding ground electrode plates, wherein the alternative arrangement of FIGS. 72 and 73 are utilized in conjunction with one another to achieve the desired blocking and filtering characteristics.
Figure 74:
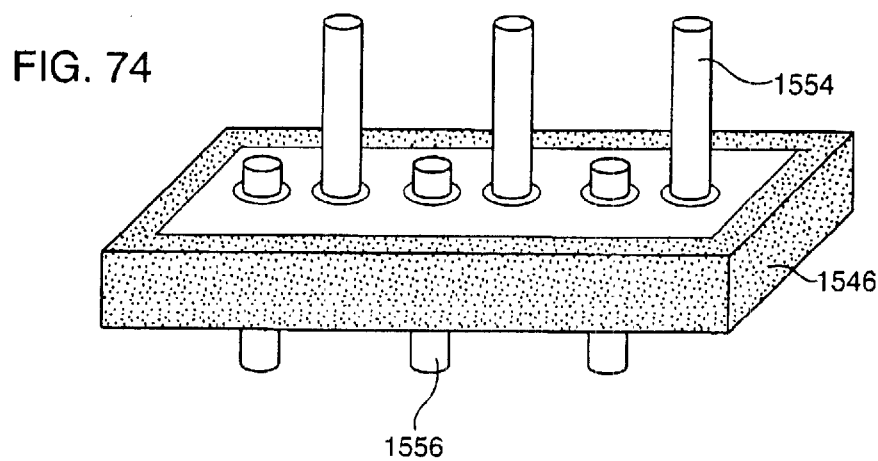
FIG. 74 is a perspective view of an integrated capacitor formed utilizing the configuration of electrode plates as shown in FIGS. 72 and 73, and further illustrating metallization around the entire perimeter of the capacitor.

The electrode plate configurations of FIGS. 72 and 73, illustrate a ground plate 1540a and 1540b which encompasses the full perimeter of the rectangular integrated capacitor 1520. FIG. 74 illustrates metallization 1546 around the entire perimeter of said capacitor 1520. In this configuration, the inductance of the ground plate is minimized, therefore optimizing the high frequency performance of the EMI feedthrough capacitor filter.

Figures 75, 76:
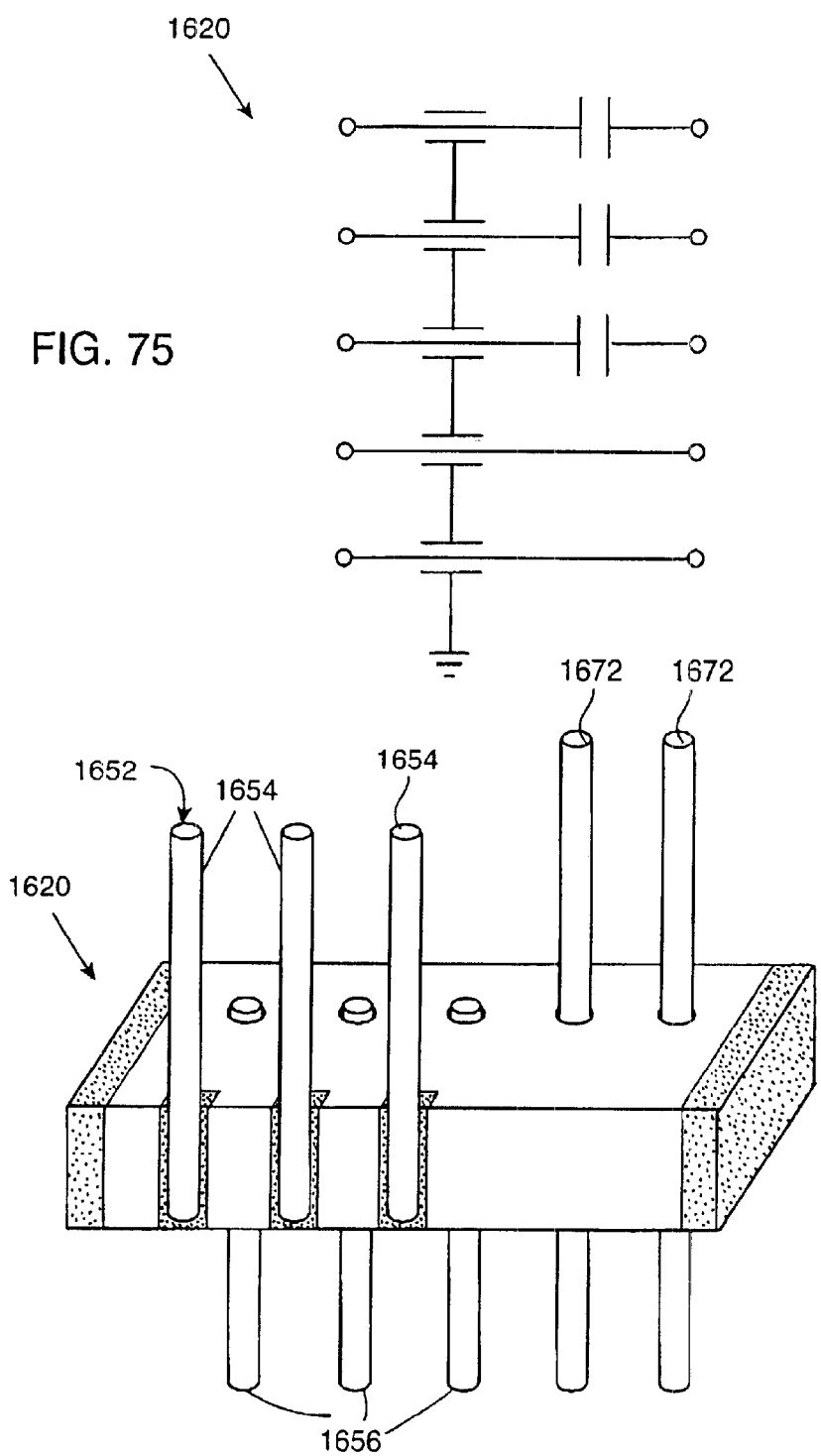
FIG. 75 is an electrical schematic diagram of a five-lead device wherein integrated DC blocking-EMI filter capacitors are provided on only three of the circuits.
FIG. 76 is a perspective view of a five-lead integrated EMI filter-DC blocking capacitor having the characteristics illustrated in the electrical schematic diagram of FIG. 75.

FIG. 75 is a schematic drawing of a five lead device showing the integrated DC blocking—EMI filter capacitors on only three of the circuits. The remaining two circuits only have feedthrough capacitor filtering for EMI protection, but not DC blocking. This is often the case in implantable medical devices where DC blocking is only required for output leads that provide a pacing pulse or other stimulus to human body tissue. On the other hand, sensing leads, such as the sensing leads for a cardiac pacemaker that monitor very low amplitude signals or cardiac waveforms, do not require DC blocking. In fact, such circuits work better when there is no series capacitance at all. The reason for this is that cardiac waveforms are relatively low in frequency and a series capacitor would have to be a very large value (in microfarads) in order that the cardiac signal not be attenuated. Therefore, it is an object of the present invention to provide DC blocking only where required and to provide optimum sensitivity on monitoring leads. It will be obvious to one skilled in the art that this can be done selectively on all or any of the drawings shown herein. That is, it is up to the capacitor designer to decide which leads require DC blocking and which leads do not.

Figure 77:
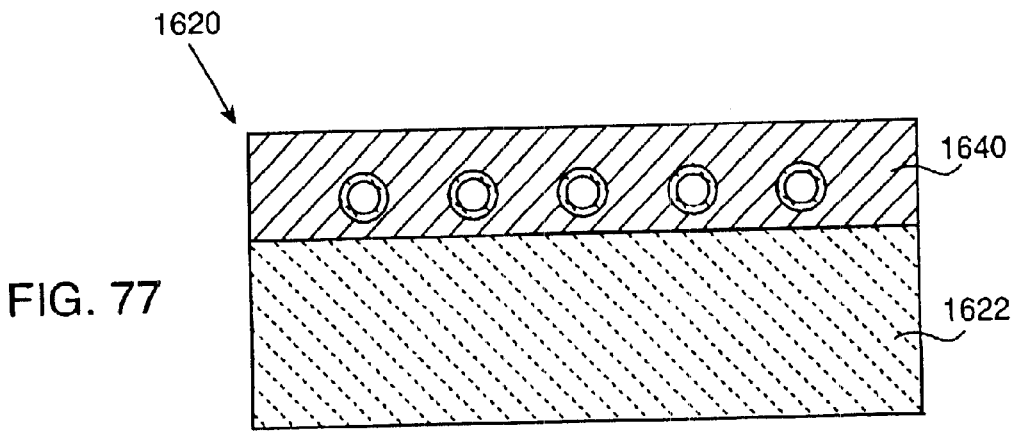
FIG. 77 is an exemplary horizontal section taken through the integrated capacitor of FIG. 76, illustrating the configuration of a ground set of electrode plates therein.
Figure 78:
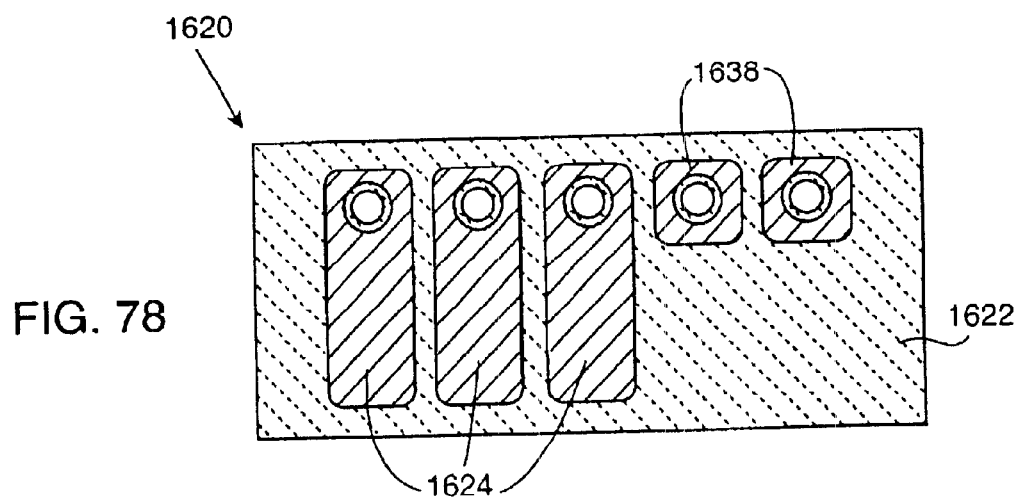
FIG. 78 is a horizontal section similar to FIG. 77, illustrating the configuration of five distinct first sets of electrode plates.
Figure 79:
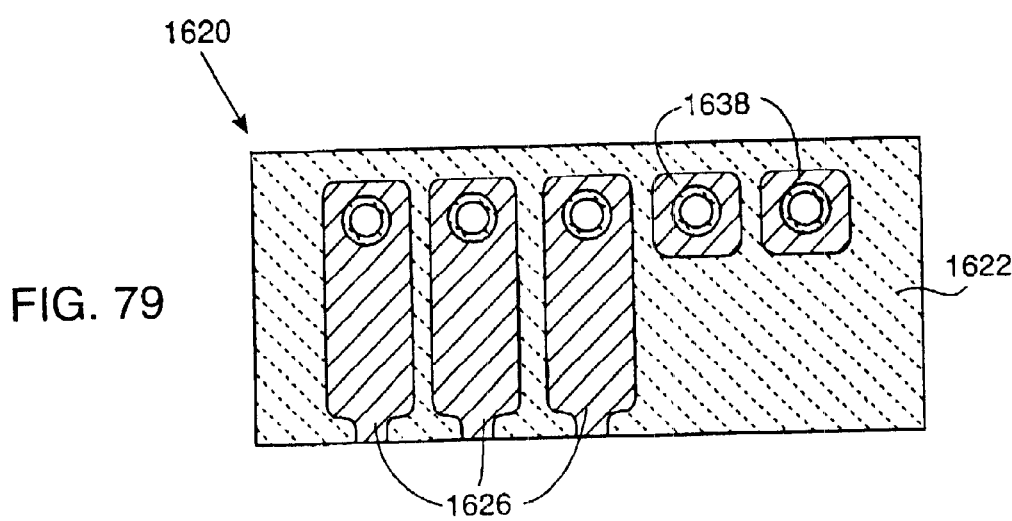
FIG. 79 is a horizontal section similar to FIG. 78, illustrating the configuration of five distinct second sets of electrode plates.

FIG. 77 illustrates the ground electrode plates 1640 of the capacitor 1620. FIG. 78 illustrates one active electrode plate set 1624, and FIG. 79 illustrates the other active electrode plate set 1626. As can be seen, in FIGS. 78 and 79, the left hand three active electrodes, when overlapped, form the DC blocking capacitance. The overlap of the three electrode plate sets with the ground plate of FIG. 77 forms an effective high frequency EMI filter capacitor. FIGS. 78 and 79 also contain two conventional feedthrough capacitors only. These are the two right hand terminals. The two right hand electrode plate sets 1638, when overlapped with the ground plates 1640 of FIG. 77, result in a high frequency EMI filter feedthrough capacitor only. Therefore, for the two right hand terminals the DC blocking capacitor has been eliminated as shown in the FIG. 75 schematic.

FIG. 80 illustrates a hermetic terminal 1750 with three lead wires 1742 (tripolar) shown on the left side of the figure. On the right side of the figure is a circuit board 1736 or substrate, which is butted up against the side of the hermetic terminal. Also shown is an integrated capacitor 1720 of the subject invention, which is shown mounted to the substrate or terminal board and buffed up against the three tripolar lead wires of the hermetic terminal. The integrated capacitor 1720 has a ground metallization stripe 1746 at its top and bottom. This ground is electrically and mechanically connected to both the hermetic terminal 1750 and the ground trace of the substrate by use of solder, conductive adhesive or the like. In a similar manner, the terminated active pads 1728, 1730 on the capacitor are connected to the solder lands of the circuit board or substrate and also to the terminal pins of the hermetic terminal. As previously described, this connection can also be made by solder, conductive adhesives or the like.

FIG. 81 is the assembly of FIG. 80 rotated 90 degrees. This rotation is provided so that the connection of the capacitor 1720 to a typical terminal pin 1742 can be seen. As can be seen, the terminal pin 1742 passes through hermetic terminal 1750 in non-conductive relation due to hermetic insulator 1751.

FIG. 82 illustrates one active electrode plate set 1724 of the capacitor 1720 of FIG. 80. FIG. 83 illustrates the other active electrode plate set 1726, and FIG. 84 illustrates a ground electrode set 1740, which runs all the way through the center of the capacitor 1720. The overlap between the active electrode plates 1724 and 1726 form the DC blocking capacitor. The overlap of both electrode plate sets 1724 and 1726 with the ground electrode plate set 1740 shown in FIG. 84, forms the high frequency EMI filter capacitor.

Figure 85:
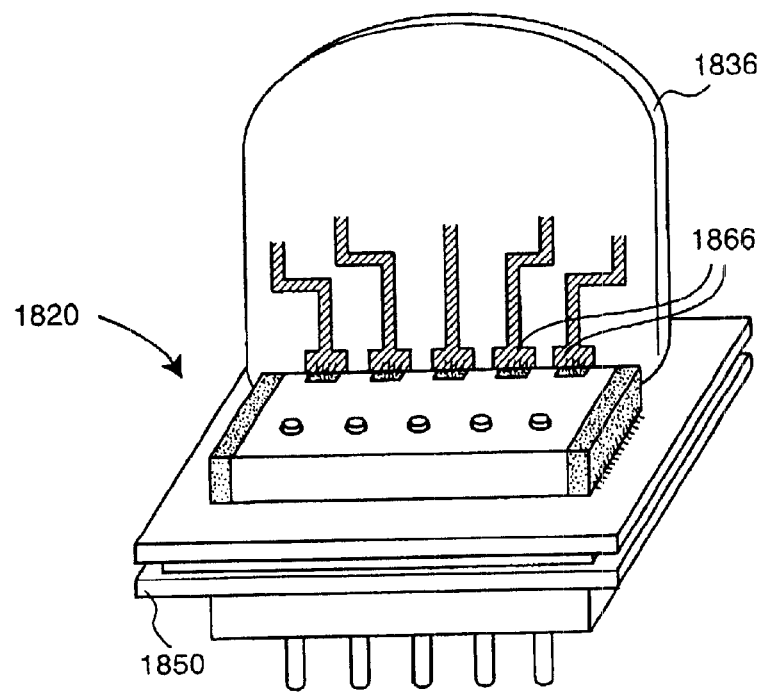
FIG. 85 is a perspective view of an alternative embodiment of the invention, wherein a substrate or circuit board is tilted on edge against the integrated capacitor.

FIGS. 85–90 illustrate yet another embodiment of an integrated capacitor 1820 embodying the present invention. In FIG. 85, a substrate or circuit board 1836 is tilted on edge up against the integrated capacitor 1820. In this case, the capacitor 1820 is bonded down to a hermetic terminal 1850 similar to the capacitor of FIG. 80. However, in this case, the circuit board 1836 is brought in at a right angle and attachments are made between the five metallized bands 1828 on the integrated capacitor to the mounting lands 1866 of the circuit board or substrate. As mentioned before, these connections can be made with solder, conductive adhesive or the like.

Figure 86:
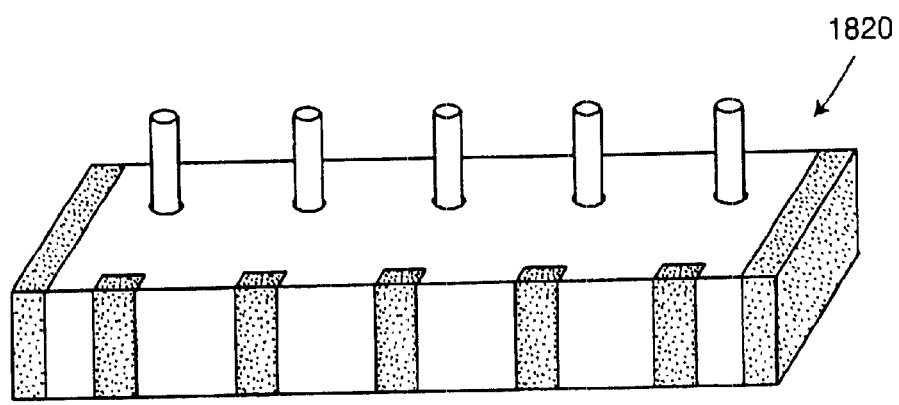
FIG. 86 is an enlarged view of the integrated capacitor of FIG. 85, which has been inverted and rotated so that it is possible to observe the lead wires coming from the hermetic terminal.
Figure 87:
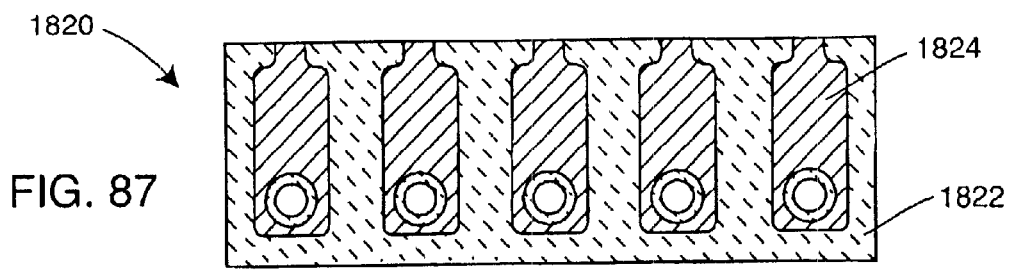
FIG. 87 is an exemplary horizontal section taken through the capacitor FIGS. 85 and 86, illustrating the configuration of five distinct first sets of electrode plates therein.
Figure 88:
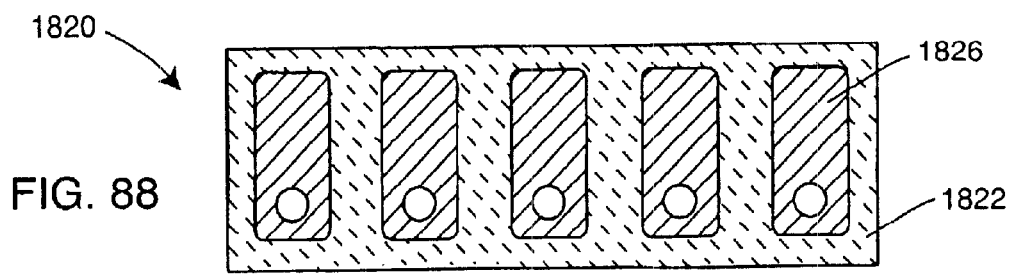
FIG. 88 is a horizontal section similar to FIG. 87, illustrating the configuration of five distinct second sets of electrode plates.
Figure 89:
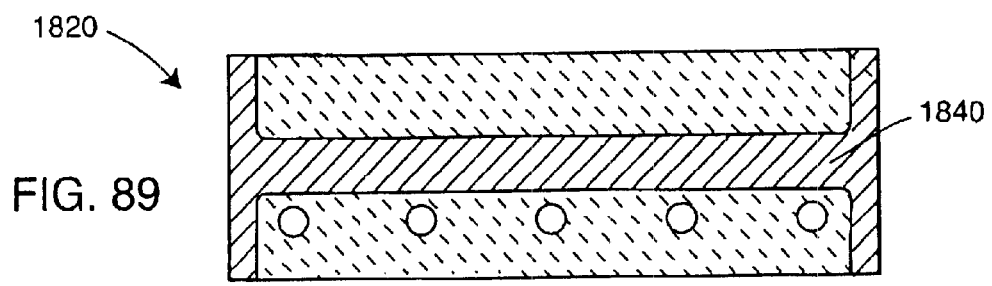
FIG. 89 is a horizontal section similar to FIGS. 87 and 88, illustrating the configuration of a set of ground electrode plates.

FIG. 86 is an enlarged view of the capacitor 1820 of FIG. 85, which has been inverted and rotated so that one can see the lead wires 1856 coming from the hermetic terminal 1850. FIG. 87 is one electrode plate set 1824, FIG. 88 illustrates the opposite electrode plate set 1826, which are connected to each one of the five lead wires, and FIG. 89 defines a ground plane 1840 running through the center of the capacitor, which is designed to have clearance from all the lead wires. The overlap of electrode plate sets 1824 and 1826 form the DC blocking capacitor. The overlap of the electrodes 1824 and 1826 with the ground electrode plate set 1840 forms the high frequency EMI filter feedthrough capacitor.

Figure 90:
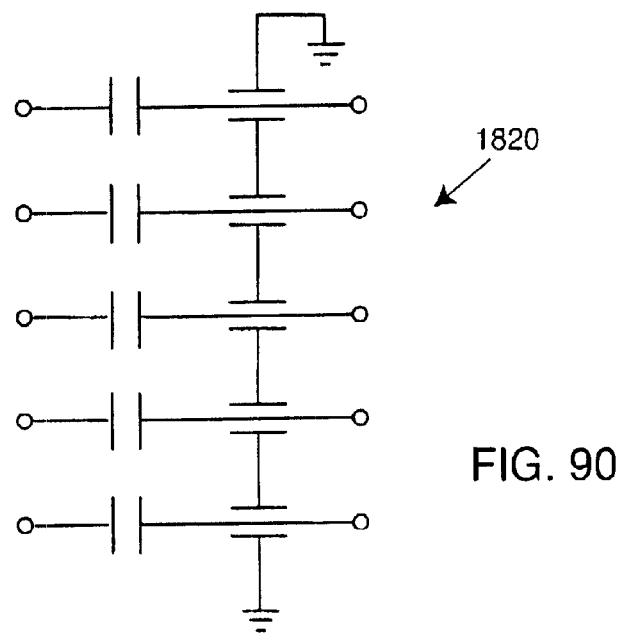
FIG. 90 is an electrical schematic diagram of the integrated EMI filter-DC blocking capacitor of FIGS. 85 and 86.

FIG. 90 is a schematic diagram of the capacitor of FIGS. 85 and 86. As mentioned before, the designer can select all of the circuits to have DC blocking, as illustrated in FIG. 90 or DC blocking can be eliminated from as many of the circuits as the designer wishes.

Figure 91:
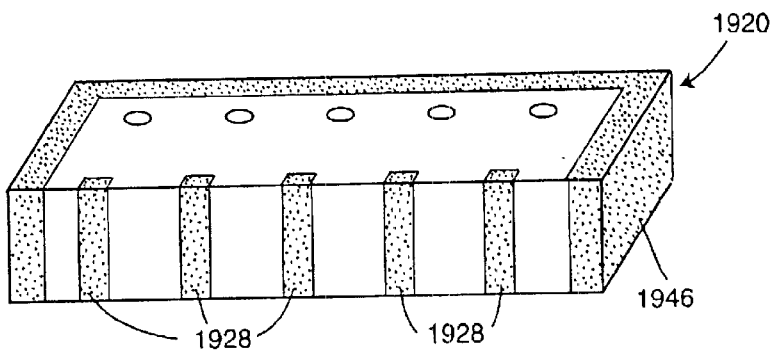
FIG. 91 is a perspective view of a variation of the capacitor of FIG. 85, wherein metallization surrounds three sides of the perimeter of the integrated capacitor.
Figure 92:
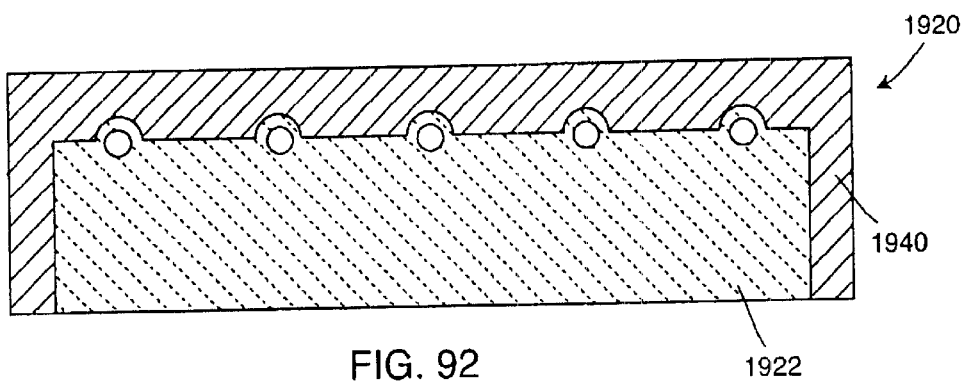
FIG. 92 is an exemplary horizontal section taken through the integrated capacitor of FIG. 91, illustrating the configuration of a ground set of electrode plates therein.
Figure 93:
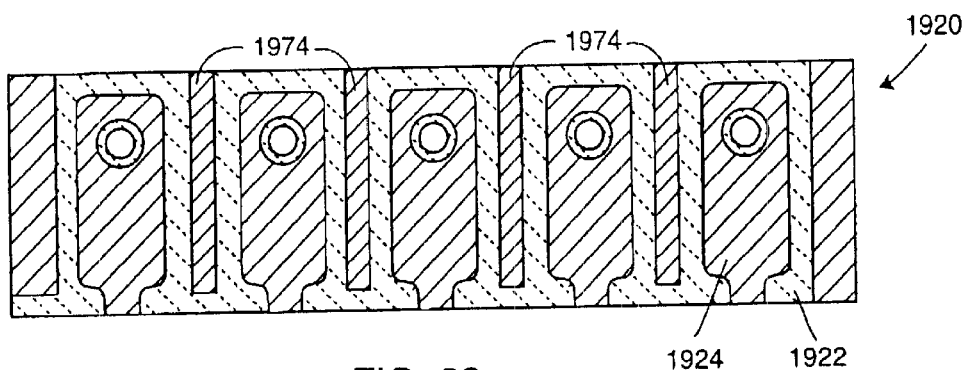
FIG. 93 is a horizontal section similar to FIG. 92, illustrating the configuration of five distinct first sets of electrode plates.
Figure 94:
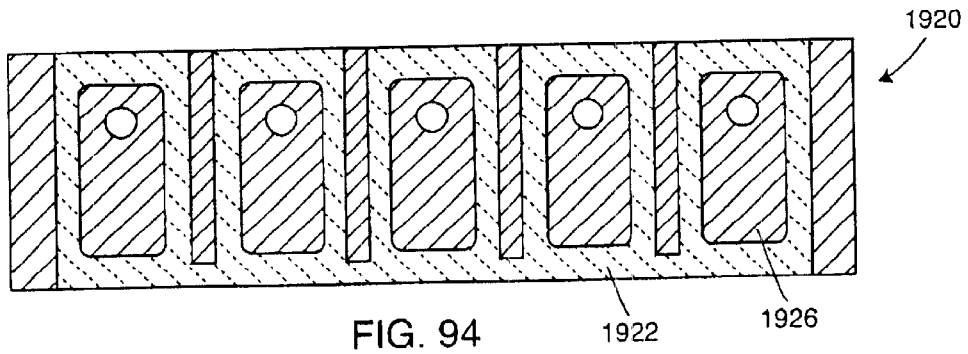
FIG. 94 is a horizontal section similar to FIG. 93, illustrating the configuration of five distinct second sets of electrode plates.
Figure 95:
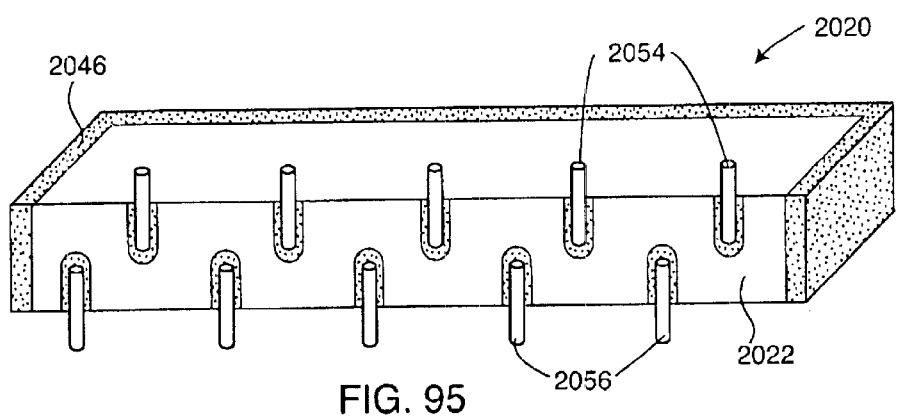
FIG. 95 is a perspective view of yet another variation of the integrated capacitor of the present invention.

FIGS. 91 through 94 illustrate yet another integrated capacitor 1920 which is similar to the integrated capacitor 1820 of FIG. 85. As can be seen in FIG. 91, there is metallization 1946 surrounding three sides of the perimeter of the integrated capacitor. FIG. 92 illustrates a ground plane 194 which extends from both ends of the capacitor all the way around its backside. FIG. 93 illustrates five active electrode plates 1924 and between these electrode plates is shown a ground electrode 1974, which forms a shield between the adjacent electrode plates. This shield 1974 is very important to eliminate the cross-talk or stray capacitance that can occur between adjacent active electrode plates. FIG. 94 is the opposite electrode plate set 1926, which is connected to the feedthrough holes. When these feedthrough holes are metallized, that effectively puts all of the active electrode plates of FIG. 94 in parallel. Referring now to FIG. 91, when the metallized stripes 1928 are placed on the capacitor 1920 as illustrated, this has the effect of putting all of the active electrode plates of FIG. 93 in parallel. The external ground metallization 1946, as illustrated on three sides of the perimeter of the capacitor 1920 in FIG. 91, has the effect of putting all of the ground electrode plates 1940 of FIG. 92 in parallel along with all of the ground stripes 1974 which shield between the active electrode plate sets of FIG. 93 and FIG. 94 in parallel. This is a preferred embodiment for all electronic devices where cross-talk is very important. One example would be for use in cochlear implant devices where a lead wire bundle is inserted into the human cochlea. These lead wires make electrical contact to the auditory nerves. It is very important that either in digital or analog stimulus applications, that cross-talk not occur between the adjacent circuits. This cross-talk would be received by the auditory nerve and human brain as undesirable noise and gibberish. It is therefore required that clean separate signals be present on each lead wire. It is a feature of the electrode plate sets 1924 and 1926 of FIGS. 93 and 94 that the active electrode plates are shielded from one another such that circuit-to-circuit parasitic capacitance is either eliminated or minimized. These shields 1974 have the desired effect of greatly reducing or even eliminating the aforementioned cross-talk. Another benefit of the electrode shield-guards 1974 of FIGS. 93 and 94 that are placed between each active electrode is that additional capacitance will then occur between each active electrode plate and ground. This has the effect of increasing the high frequency EMI filter (feedthrough capacitor) performance which works by decoupling undesirable interference to ground.

Figure 96:
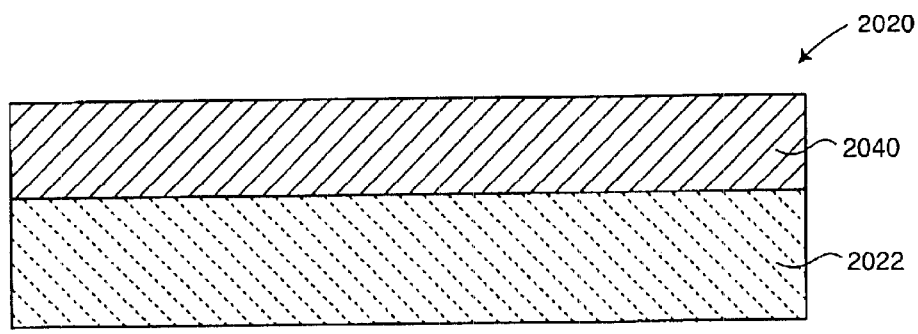
FIG. 96 is an exemplary horizontal section taken through the capacitor of FIG. 95, illustrating the configuration of a ground set of electrode plates therein.
Figure 97:
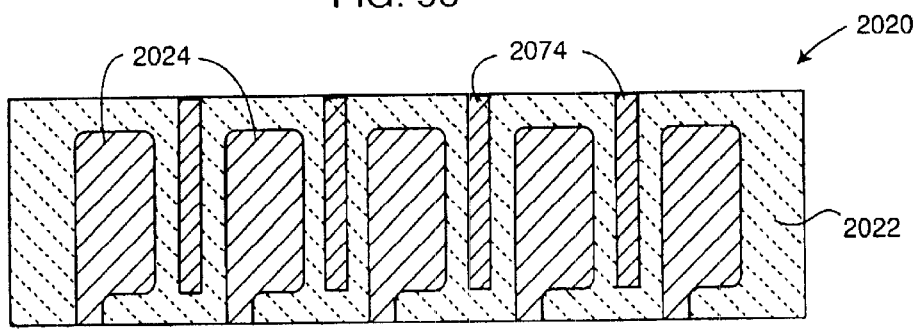
FIG. 97 is a horizontal section similar to FIG. 96, illustrating the configuration of five distinct first sets of electrode plates.
Figure 98:
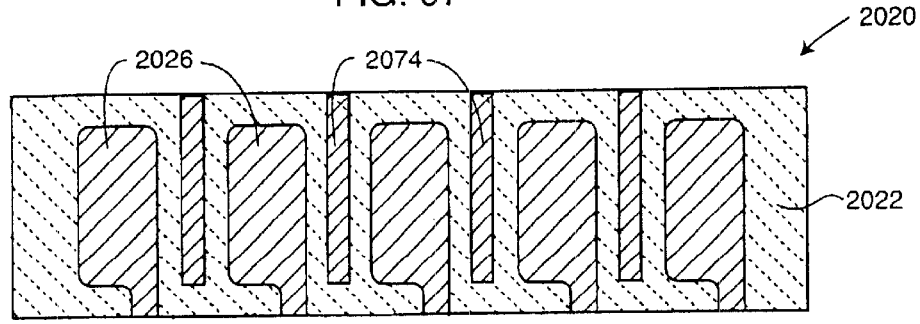
FIG. 98 is a horizontal section similar to FIGS. 96 and 97, illustrating the configuration of five distinct second sets of electrode plates.

FIGS. 95 through 98 illustrate yet another variation showing in this case, lead wires coming up from the bottom and then exiting from the top. FIG. 96 illustrates one type of ground plane 2040 possible for the integrated capacitor 2020 of FIG. 95. FIG. 97 illustrates the active electrode plate set 2024 that would connect to the bottom lead wires 2056 of FIG. 95. As can be seen, there are ground shields 2074 present between each of the active electrodes to minimize or prevent cross-talk. FIG. 98 is the opposite electrode plate set 2026, which is designed to be connected to the upper lead wires 2054 of FIG. 95. As in FIG. 97, there are ground shields 2074 placed between the active electrode plates.

FIG. 99 illustrates the hermetic terminal 2150 of a cardiac pacemaker, implantable cardioverter defibrillator, neurostimulator, or other implantable medical device. The hermetic terminal 2150 is typically formed of a metal such as titanium, which is highly resistant to corrosion by body fluids. Each of the five foreground lead wires 2156 illustrated in FIG. 99 passes through the hermetic terminal 2150 in non-conductive (insulative) relation. The foreground leads are hermetically sealed into the titanium ferrule either by compression glass sealing, fusion glass sealing, or by the use of brazed alumina insulators or the like. The integrated DC blocking—EMI filter capacitor 2120 of FIG. 99 is then placed over the five terminals of the hermetic terminal. As shown in FIG. 99, these are the five terminals 2156 in the foreground that only extend a small distance (or not at all) through the integrated capacitor. The other five lead wires 2154 that are shown towards the back of FIG. 99, go to the inside of the implantable medical device and can be routed to various circuits or substrates.

FIG. 100 is one active electrode plate set 2126 of the capacitor 2120 of FIG. 99. As can be seen, there are ground shields between each of the active electrodes to prevent cross-talk. FIG. 101 is the opposite electrode plate set 2124. In this case, these electrodes are designed to connect to the lead wires 2154 that go to the inside of the medical device. In contrast, the electrodes 2126 of FIG. 100 are designed to connect to the five terminal pins 2156 coming from the hermetic terminal 2150. FIG. 102 is one ground plane 2140

(many are possible) of the capacitor 2120 of FIG. 99. The capacitor 2120 is metallized 2146 around its entire perimeter thereby minimizing the inductance to the internal ground plates. This has the effect of both maximizing the EMI feedthrough filter capacitor to ground and also maximizing the shielding between the adjacent electrode plate sets.

A disadvantage of the installation as shown in FIG. 99 is that this type of installation tends to subject the integrated capacitor 2120 to very high thermal and mechanical stresses. This is because the hermetic terminal 2150 is designed to be installed into the titanium housing of an implantable medical device by laser welding. This welding occurs in very close proximity to the integrated capacitor thereby causing a very rapid temperature rise around the perimeter of the capacitor. This causes two very undesirable effects. First of all, the capacitor can be easily damaged by the thermal shock caused by the high rate of heat rise. Thermal shock alone can be damaging to a monolithic thermal capacitor resulting in micro cracks or even major cracks or delaminations. Another way cracking can be introduced in the capacitor is through mechanical stress. In this case, the thermal coefficient of expansion (TCE) of the titanium ferrule and that of the relatively brittle ceramic capacitor does not match. During laser welding, the titanium ferrule expands at a much greater rate than the ceramic capacitor. This puts enormous tensile strength into the capacitor, which is primarily barium titanate based. Barium titanate capacitor dielectric material is relatively strong in compression, but very weak in tension. Accordingly, mismatches in coefficient of expansion and resultant mechanical stress can also induce cracks. Cracks are highly undesirable in a monolithic ceramic capacitor since they can lead to latent failure of the device. These latent failures can be due to migration of the various materials and metals used in a capacitor electrodes and metallization, or through moisture penetration, use of solvents or other contaminants that may penetrate to the inside of the capacitor. Typical failure mechanisms include low insulation resistance, high voltage failure, or short-circuiting. Severe cracking can even cause loss of capacitance and increased dissipation factor.

Figure 103:
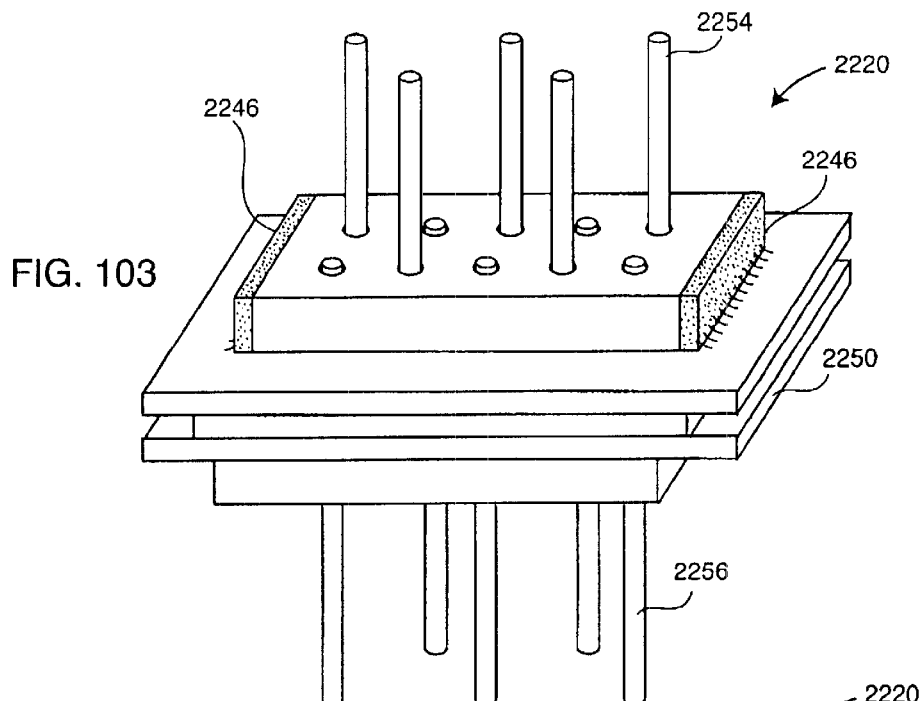
FIG. 103 is a perspective view of a similar assembly to that shown in FIG. 99, wherein the integrated capacitor is metallized on its two opposed ends which are, in turn, connected to a conductive substrate only in these two locations.

FIG. 103 is a similar assembly to the assembly of FIG. 99. In FIG. 103 it can be seen that the capacitor 2220 is metallized 2246 on its two opposed ends and in turn connected to the titanium ferrule 2250 only in these two locations. This tends to reduce both the thermal and the mechanical stress to the capacitor 2220 by providing a reduced contact area and therefore, less heat flow. There is still a significant problem remaining in that the titanium ferrule will expand at greater rate than the capacitor itself thereby inducing tensile stress into the capacitor's structure. The capacitor of FIG. 103 has a staggered lead wire pattern.

Figure 104:
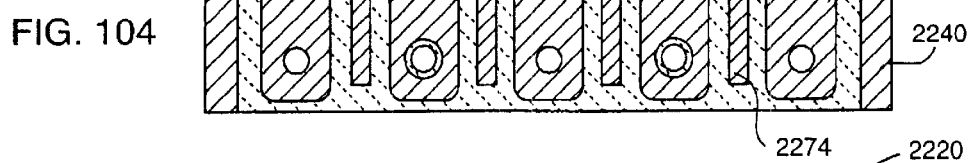
FIG. 104 is an exemplary horizontal section taken through the integrated capacitor of FIG. 103, illustrating the configuration of five distinct first sets of electrode plates and a set of ground electrode plates therein.

FIG. 104 illustrates an active electrode plate set 2226, which alternates from lead to lead. This active electrode plate set 2226 is designed to connect to the five lead wires 2256 coming through the hermetic terminal 2250.

Figure 105:
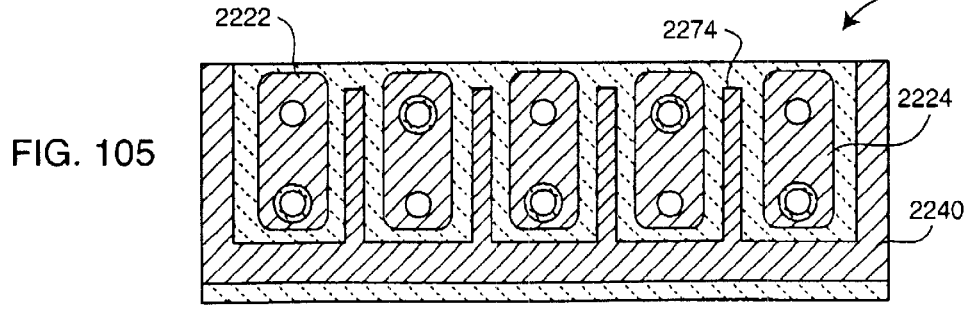
FIG. 105 is a horizontal section similar to FIG. 104, illustrating the configuration of five distinct second sets of electrode plates and the set of ground electrode plates.

FIG. 105 is the opposite electrode plate set 2224, which is designed to connect to the five lead wires 2254 going to the inside of the implantable medical device. As can be seen, the ground electrode plates 2240 of FIG. 104 and FIG. 105 only penetrate to the capacitor outside on its opposite ends. It will be obvious to one skilled in the art that a number of other embodiments for the ground electrode plate are possible, including having the electrode come out in a couple of locations along the capacitors sides, or a combination of sides and ends. The ground electrode plates of FIG. 104 and FIG. 105 employ grounded shields 2274 between the active electrode plates to minimize or eliminate cross-talk.

Figure 106:
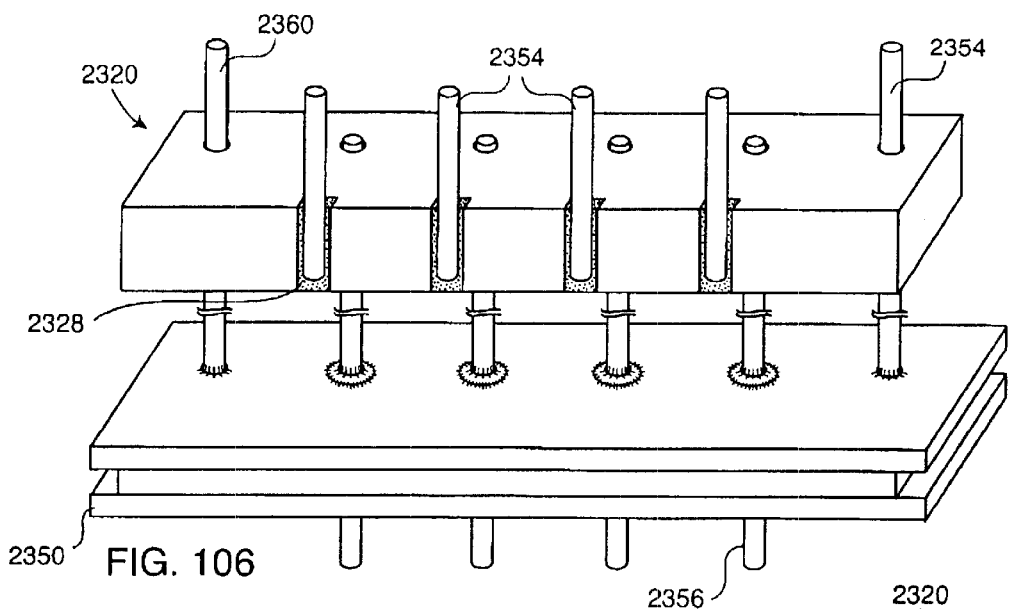
FIG. 106 illustrates another alternative embodiment of an integrated capacitor embodying the present invention utilizing two internally grounded pins.

FIG. 106 illustrates another preferred embodiment that is mounted to a hermetic terminal 2350 like the capacitor of FIG. 99. Importantly, in the integrated capacitor 2320 of FIG. 106, there is no external perimeter metallization to the capacitor and also no perimeter connection to the capacitor's ground electrode plate. In this case, there are two (or more) grounded pins 2360 that are connected by welding, brazing or the like, directly to the titanium ferrule 2350 of the hermetic seal. The capacitor 2320 of FIG. 106 is shown just prior to assembly where it would be pushed down and mated against the ferrule of the hermetic terminal. As can be seen, the two outer most terminal pins 2360 coming through the hermetic terminal 2350 are directly attached and grounded to the hermetic terminal itself. The center four (quad polar) leads 2356 pass through the hermetic terminal in insulative, but hermetic relationship. There is also a spacer washer (not shown), which is nonconductive that would sandwich in between the top of the hermetic terminal and the integrated capacitor. The purpose of this thin insulating washer is to make sure that the four metallization pads 2328 on the front side of the capacitor 2320 do not touch against the titanium ferrule 2350 and short out the quad polar lead wires. Accordingly, the integrated DC blocking—EMI feedthrough capacitor 2320 is of the internally grounded type described in U.S. Pat. No. 5,905,627, the contents of which are incorporated herein.

Figure 107:
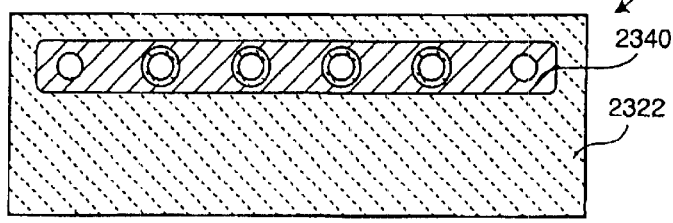
FIG. 107 is an exemplary horizontal section taken through the integrated capacitor of FIG. 106, illustrating the configuration of a ground set of electrode plates therein.
Figure 108:
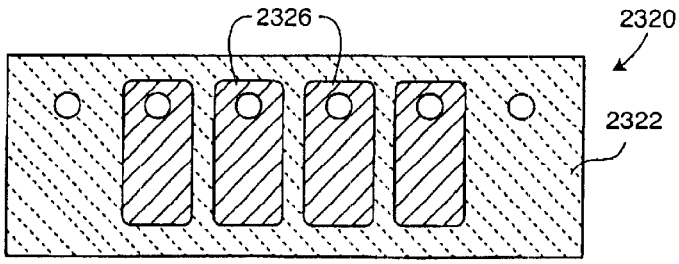
FIG. 108 is a horizontal section similar to FIG. 107, illustrating the configuration of four distinct first sets of electrode plates.
Figure 109:
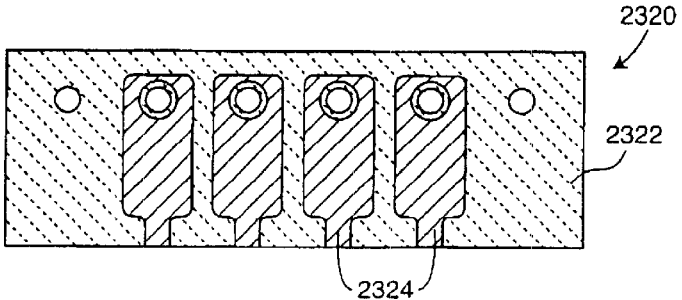
FIG. 109 is a horizontal section similar to FIGS. 107 and 108, illustrating the configuration of four distinct second sets of electrode plates.

FIG. 107 is an illustration of an internally grounded ground electrode plate set 2340, which is connected to the two outer most terminals pins 2360 and then runs across the capacitor. FIG. 108 illustrates one active electrode plate set 2326, which is designed to connect to the four (quad polar) terminals that come through the hermetic terminal. FIG. 109 is the other electrode plate set 2324, which is designed to connect to metallized pads 2328 on the front of the capacitor 2320. It will be obvious to one skilled in the art that these electrodes could be made in many possible configurations, either with feedthrough holes or with metallized pads as shown in previous drawings. The advantage of the capacitor 2320 as illustrated in FIG. 106 is that there is no attachment between the perimeter of the capacitor and the titanium ferrule 2350. Accordingly, this eliminates the thermal shock and mechanical stress to the capacitor that would have occurred during installation by laser welding or other temperature excursions.

Figure 110:
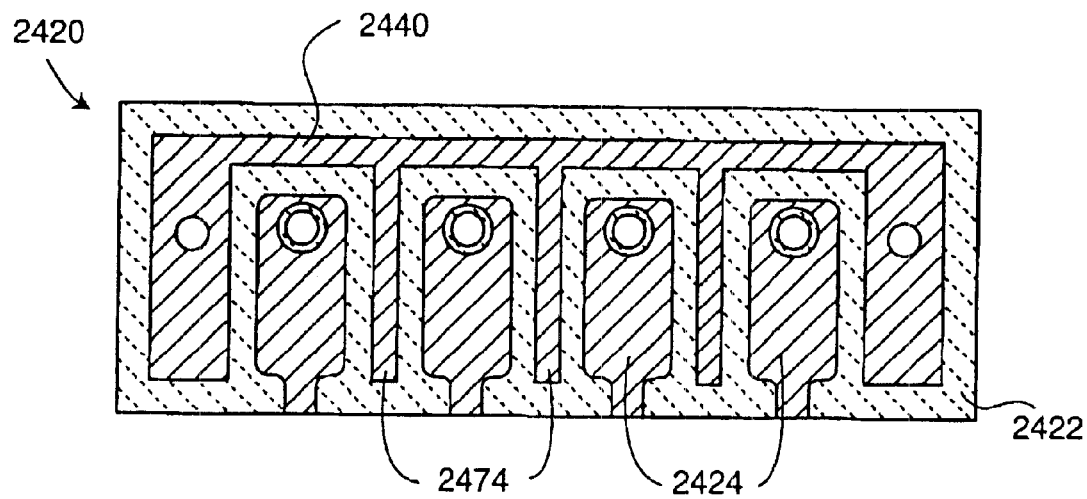
FIG. 110 is a horizontal section similar to FIG. 109, which has been modified to include ground shields between the second sets of electrode plates to eliminate cross-talk.

FIG. 110 illustrates the electrode plate set of FIG. 109 with the addition of ground shields 2474 between the active electrode plates 2424 to eliminate cross-talk.

Figure 111:
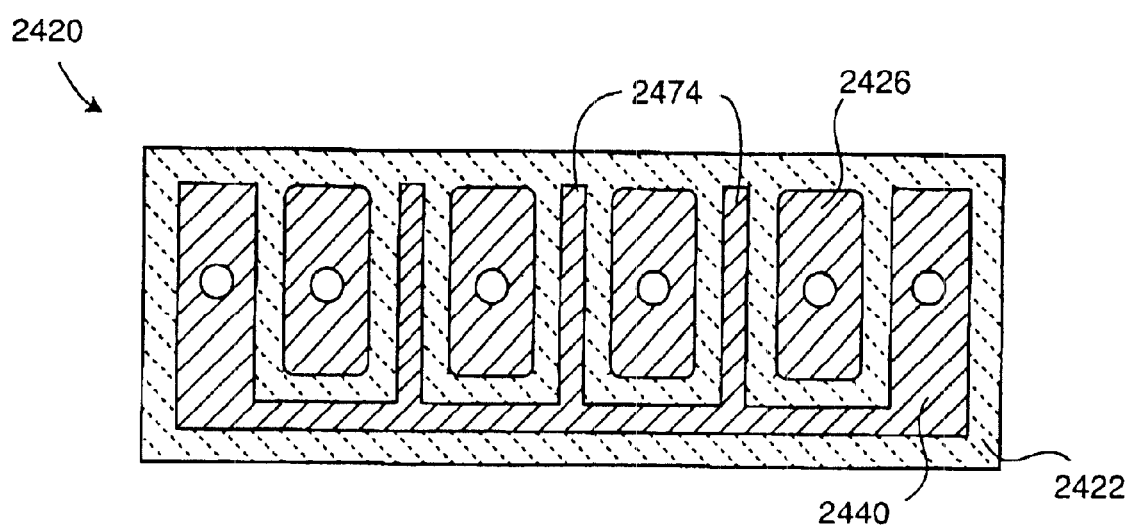
FIG. 111 is a horizontal section similar to FIG. 108, with ground shields added to eliminate cross-talk.

FIG. 111 is the electrode plate set of FIG. 108, again with ground shields 2474 added to eliminate cross-talk. A desirable feature in the electrode plate sets 2424 and 2426 of FIG. 110 and FIG. 111 is that this minimizes the amount of silk screening and stacking as the capacitor 2420 is manufactured. This is because all of the electrodes are contained in two manufacturing lay ups. The overlap of the active electrodes 2424 and 2426 between FIG. 110 and FIG. 111 create the DC blocking capacitor. The overlap of the active 2424 electrodes of FIG. 110 with the ground electrode 2440 of FIG. 111 create the EMI filter capacitor. In a like manner, the four active electrode plates 2426 of FIG. 111, when they overlay the ground electrode 2440 of FIG. 110, also create additional EMI feedthrough capacitance to ground.

Although several embodiments of the invention have been described in detail for purposes of illustration, various further modifications may be made without departing from the spirit and the scope of the invention. Accordingly, the invention is not limited except by the appended claims.

I claim:

1. A capacitor, comprising:
   a monolithic casing of ceramic dielectric material;
   first and second sets of electrode plates disposed within the monolithic casing to form a DC blocking capacitor; and
   ground electrode plates disposed within the monolithic casing and between selected portions of the first and second sets of electrode plates to form an electromagnetic interference (EMI) filter.

2. The capacitor of claim 1, including a first conductive band on a surface of the casing for conductively coupling the first set of electrode plates, a second conductive band on a surface of the casing for conductively coupling the second set of electrode plates, and a third conductive band on the surface of the casing for conductively coupling the ground electrode plates.

3. The capacitor of claim 2, wherein the first, second and third conductive bands are disposed on exterior surfaces of the casing.

4. The capacitor of claim 1, wherein the first and second sets of electrode plates include an induction-inducing material.

5. The capacitor of claim 4, wherein the induction-inducing material includes nickel.

6. The capacitor of claim 1, including a discontinuous lead wire extending at least partially into the casing, wherein a first segment of the lead wire is conductively coupled to the first set of electrode plates, and a second segment of the lead wire is conductively coupled to the second set of electrode plates.

7. The capacitor of claim 6, including an insulative spacer disposed between abutting ends of the first and second segments of the lead wire within the casing.

8. The capacitor of claim 6, wherein the ground electrode plates are conductively coupled to a conductive ferrule through which a portion of the lead wire extends in non-conductive relation.

9. The capacitor of claim 1, wherein the first and second sets of electrode plates form a plurality of distinct DC blocking capacitors, and wherein the ground electrode plates cooperatively form, with the first and second sets of electrode plates, an EMI filter for each of the distinct DC blocking capacitors.

10. The capacitor of claim 9, including a discontinuous lead wire corresponding to each of the distinct DC blocking capacitors and extending at least partially into the casing, wherein a first segment of the lead wire is conductively coupled to the first set of electrode plates, and a second segment of the lead wire is conductively coupled to the second set of electrode plates.

11. The capacitor of claim 10, wherein the ground electrode plates are conductively coupled to a conductive ferrule through which a portion of the lead wire extends in non-conductive relation.

12. The capacitor of claim 11, including a conductive band on an external surface of the casing for conductively coupling the ground electrode plates to the conductive ferrule.

13. The capacitor of claim 11, including a conductive band on an internal surface of the casing for conductively coupling the ground electrode plates to the conductive ferrule.

14. The capacitor of claim 13, including a ground pin conductively coupled to the ferrule and to the conductive band.

15. The capacitor of claim 9, including a plurality of first conductive bands on a surface of the casing corresponding to the distinct DC blocking capacitors for conductively coupling the first sets of electrode plates, second conductive bands corresponding to the distinct DC blocking capacitors and on a surface of the casing for conductively coupling the respective second sets of electrode plates, and a third conductive band on a surface of the casing for conductively coupling the ground electrode plates.

16. The capacitor of claim 10, wherein ends of the first and second segments of the lead wire are disposed in passageways provided in the casing.

17. The capacitor of claim 16, wherein the passageways comprise through-holes.

18. The capacitor of claim 17, wherein an end of each of the first and second segments is covered with a non-conductive cap.

19. The capacitor of claim 10, wherein the ground electrode plates are aligned with the first and second segments of the lead wire extending into the casing.

20. The capacitor of claim 10, wherein the ground electrode plates are offset from the first and second segments of the lead wire extending into the casing.

21. The capacitor of claim 9, wherein the ground electrode plates comprise a first set of ground electrode plates which are co-planar with the first set of electrode plates, and a second set of ground electrode plates which are co-planar with the second set of electrode plates.

22. The capacitor of claim 21, including a conductive band on an external surface of the casing for conductively coupling the ground electrode plates to a conductive ferrule.

23. The capacitor of claim 22, wherein the conductive band surrounds the casing.

24. The capacitor of claim 9, including a third set of electrode plates forming an EMI filter, cooperatively with the ground electrode plates, for a lead wire extending through the casing and conductively coupled to the third set of electrode plates.

25. The capacitor of claim 9, including a grounded shield electrode plate co-planarly disposed between adjacent components of the first set of electrode plates to reduce cross-talk therebetween.

26. The capacitor of claim 9, including a grounded shield electrode plate cooperatively disposed between adjacent components of the second set of electrode plates to reduce cross-talk therebetween.

27. An integrated electromagnetic interference (EMI) filter-DC blocking capacitor, comprising:
   a casing of dielectric material having first and second sets of electrode plates disposed therein forming a DC blocking capacitor;
   a first conductive band on a surface of the casing for conductively coupling the first set of electrode plates;
   a second conductive band on a surface of the casing for conductively coupling the second set of electrode plates;
   a set of ground electrode plates disposed within the casing between selected portions of adjacent plates of the first and second sets of electrode plates; and
   a third conductive band on a surface of the casing for conductively coupling the set of ground electrode plates.

28. The capacitor of claim 27, wherein the first and second sets of electrode plates include an induction-inducing material.

29. The capacitor of claim 28, wherein the induction-inducing material includes nickel.

30. The capacitor of claim 27, including a discontinuous lead wire extending at least partially into the casing, wherein a first segment of the lead wire is conductively coupled to the first set of electrode plates, and a second segment of the lead wire is conductively coupled to the second set of electrode plates.

31. The capacitor of claim 30, including an insulative spacer disposed between abutting ends of the first and second segments of the lead wire within the casing.

32. The capacitor of claim 30, wherein the ground electrode plates are conductively coupled to a conductive ferrule through which a portion of the lead wire extends in non-conductive relation.

33. The capacitor of claim 27, wherein the first and second sets of electrode plates form a plurality of distinct DC blocking capacitors, and wherein the ground electrode plates cooperatively form, with the first and second sets of electrode plates, an EMI filter for each of the distinct DC blocking capacitors.

34. The capacitor of claim 33, including a discontinuous lead wire corresponding to each of the distinct DC blocking capacitors and extending at least partially into the casing, wherein a first segment of the lead wire is conductively coupled to the first set of electrode plates, and a second segment of the lead wire is conductively coupled to the second set of electrode plates.

35. The capacitor of claim 34, wherein the ground electrode plates are conductively coupled to a conductive ferrule through which a portion of the lead wire extends in non-conductive relation.

36. The capacitor of claim 35, including a conductive band on an external surface of the casing for conductively coupling the ground electrode plates to the conductive ferrule.

37. The capacitor of claim 35, including a conductive band on an internal surface of the casing for conductively coupling the ground electrode plates to the conductive ferrule.

38. The capacitor of claim 37, including a ground pin conductively coupled to the ferrule and to the conductive band.

39. The capacitor of claim 34, wherein ends of the first and second segments of the lead wire are disposed in passageways provided in the casing.

40. The capacitor of claim 34, wherein the ground electrode plates are aligned with the first and second segments of the lead wire extending into the casing.

41. The capacitor of claim 34, wherein the ground electrode plates are offset from the first and second segments of the lead wire extending into the casing.

42. The capacitor of claim 37, wherein the ground electrode plates comprise a first set of ground electrode plates which are co-planar with the first set of electrode plates, and a second set of ground electrode plates which are co-planar with the second set of electrode plates.

43. The capacitor of claim 42, including a conductive band on an external surface of the casing for conductively coupling the ground electrode plates to the conductive ferrule.

44. The capacitor of claim 27, including a third set of electrode plates forming an EMI filter, cooperatively with the ground electrode plates, for a lead wire extending through the casing and conductively coupled to the third set of electrode plates.

45. The capacitor of claim 33, including a grounded shield electrode plate co-planarly disposed between adjacent components of the first set of electrode plates to reduce cross-talk therebetween.

46. The capacitor of claim 33, including a grounded shield electrode plate cooperatively disposed between adjacent components of the second set of electrode plates to reduce cross-talk therebetween.

47. An integrated electromagnetic interference (EMI) filter-DC blocking capacitor, comprising:

a casing of dielectric material having generally parallel first and second sets of electrode plates disposed therein which form a plurality of distinct DC blocking capacitors; and a set of generally parallel ground electrode plates disposed within the casing between selected portions of adjacent plates of the first and second sets of electrode plates, the ground electrode plates cooperatively forming, with the first and second sets of electrode plates, an EMI filter for each of the distinct DC blocking capacitors.

48. The capacitor of claim 47, wherein the first and second sets of electrode plates include an induction-inducing material.

49. The capacitor of claim 47, including a discontinuous lead wire corresponding to each of the distinct DC blocking capacitors and extending at least partially into the casing, wherein a first segment of the lead wire is conductively coupled to the first set of electrode plates, and a second segment of the lead wire is conductively coupled to the second set of electrode plates.

50. The capacitor of claim 49, wherein the ground electrode plates are conductively coupled to a conductive ferrule through which a portion of the lead wire extends in non-conductive relation.

51. The capacitor of claim 49, including a conductive band on an external surface of the casing for conductively coupling the ground electrode plates to the conductive ferrule.

52. The capacitor of claim 51, including a grounded shield electrode plate co-planarly disposed between adjacent components of the first set of electrode plates to reduce cross-talk therebetween.

53. The capacitor of claim 51, including a grounded shield electrode plate cooperatively disposed between adjacent components of the second set of electrode plates to reduce cross-talk therebetween.

54. The capacitor of claim 53, wherein the ground electrode plates comprise a first set of ground electrode plates which are co-planar with the first set of electrode plates, and a second set of ground electrode plates which are co-planar with the second set of electrode plates.

55. The capacitor of claim 50, including a conductive band on an internal surface of the casing for conductively coupling the ground electrode plates to the conductive ferrule, including a ground pin conductively coupled to the ferrule and to the conductive band.

56. The capacitor of claim 47, including a third set of electrode plates forming an EMI filter, cooperatively with the ground electrode plates, for a lead wire extending through the casing and conductively coupled to the third set of electrode plates.

* * * * *